(12) United States Patent
Cho et al.

(10) Patent No.: US 8,246,962 B2
(45) Date of Patent: Aug. 21, 2012

(54) CANINE INFLUENZA VIRUS AND VACCINE THEREFORE

(75) Inventors: Young Shik Cho, Suwon-si (KR); Gun Woo Ha, Seoul (KR); Jin Sik Oh, Suwon-si (KR); Dong Seok Kang, Suwon-si (KR); Dae Sub Song, Suwon-si (KR); Bo Kyu Kang, Suwon-si (KR); Chul Seung Lee, Seoul (KR)

(73) Assignee: Bionote Inc., Hwaseong-Si, Gyeonggi-Do (KR)

( * ) Notice: Subject to any disclaimer, the term of this patent is extended or adjusted under 35 U.S.C. 154(b) by 0 days.

(21) Appl. No.: 12/375,924

(22) PCT Filed: Nov. 16, 2007

(86) PCT No.: PCT/KR2007/005789
§ 371 (c)(1),
(2), (4) Date: Apr. 16, 2009

(87) PCT Pub. No.: WO2009/057843
PCT Pub. Date: May 7, 2009

(65) Prior Publication Data
US 2010/0285063 A1    Nov. 11, 2010

(30) Foreign Application Priority Data
Oct. 30, 2007 (KR) .................. 10-2007-0109535

(51) Int. Cl.
*A61K 39/145* (2006.01)
(52) U.S. Cl. ............. 424/209.1; 424/184.1; 424/204.1; 424/186.1; 435/5
(58) Field of Classification Search ............ None
See application file for complete search history.

(56) References Cited

U.S. PATENT DOCUMENTS

| 6,605,457 | B1 |   | 8/2003 | Fiers et al. |           |
|-----------|----|---|--------|--------------|-----------|
| 7,052,701 | B2 | * | 5/2006 | Barrett et al. | 424/199.1 |
| 7,722,884 | B2 | * | 5/2010 | Shields et al. | 424/209.1 |

OTHER PUBLICATIONS

GenBank Accession # AAW78047, hemagglutinin [Influenza A virus (A/chicken/Korea/S6/03(H3N2))]., 2005.*
GenBank Accession # AY862639 Influenza A virus (A/chicken/Korea/S6/03(H3N2)) neuraminidase (NA) gene, complete cds., 2005.*
GenBank Accession # AAW78-79, neuraminidase [Influenza A virus (A/chicken/Korea/S6/03(H3N2))], 2005.*
World Health Organization, Weekly Epidemiological Record, Feb. 28, 1997, vol. 72, pp. 57-64.*
GenBank Accession# AAB66792, hemagglutinin, partial [Influenza A virus (A/Nanchang/933/95(H3N2))], 1997.*
GenBank Accession# CAD29973, neuraminidase [Influenza A virus (A/Nanchang/933/95(H3N2))], 2005.*
European Search Report to PCT/KR2007/005789, 2009.
Song Daesub et al., "Transmission of avian influenza virus (H3N2) to dogs", Emerging Infectious Diseases, vol. 14, No. 5, May 2008, pp: 741-746.
Choi Y K et al., "Avian influenza viruses in Korean live poultry markets and their pathogenic potential", Virology, vol. 332, No. 2, Feb. 20, 2005, pp: 529-537.
International Search Report to PCT/KR2007/005789, 2008.
Influenza A virus hemagglutinin gene, complete cds, NCBI GenBank Accession AY862607 (Feb. 7, 2005).
Influenza A virus hemagglutinin gene, complete cds, NCBI GenBank Accession AY862641 (Feb. 7, 2005).
Kristin L Nichol et al., "Vaccine for seasonal and pandemic influenza", The Journal of Infectious Disease, Nov. 2006, vol. 194, pp. 111-118.

* cited by examiner

*Primary Examiner* — Benjamin P Blumel
(74) *Attorney, Agent, or Firm* — Knobbe, Martens, Olson & Bear, LLP

(57) ABSTRACT

Novel influenza viruses A/Canine/Korea/01/07 (H3N2), A/Canine/Korea/02/07 (H3N2) and A/Canine/Korea/03/07 (H3N2) are disclosed. A vaccine composition comprising at least one of the viruses, a method for preventing or treating diseases resulting from influenza virus infection by administering the vaccine composition, and an assay kit for detecting the viruses are also disclosed.

14 Claims, 7 Drawing Sheets

Figure 1

```
                    10         20         30         40         50
                    |          |          |          |          |
1. A/Canine/Korea/01/07(H3N2)  MNPNQKIIAIGSVSLTIATVCFLLQIAILATTVTLHFKQNECNIPSNSQVVPCKP
2. A/Dove/Korea/S11/03(H3N2)   ...................M..............G.S....N.......E.
3. A/Duck/Korea/S7/03(H3N2)    ...................M..............G.S....N.......E.
4. A/Chicken/Korea/S6/03(H3N2) ...................M..............G.S....N.......E.

60         70         80         90        100        110        120        130
       |          |          |          |          |          |          |          |
1. VVPCKPIIERNITEVVYLNNTTIEKEICSIVLEYRNWSKPQCQITGFAPFSKDNSIRLSAGGDIWVTREPYVSCDPSKCYQ]
2. ...E.T...............V....PGMP..........................................
3. ...E.T...............V....PGMP..........................................
4. ...E.T...............V....PGMP.....W....V.........F.....................

140        150        160        170        180        190        200        210
       |          |          |          |          |          |          |          |
1. YQFALGQGTTLNNKHSNGTIHDRISHRTLLMNELGVPFHLGTKQVCIAWSSSSCHDGKAWLHVCVTGDDRNATASFVYNGMLV
2. .............D..P...............................................S.......I.D
3. .............D.E.P..............................................S.......I.D
4. .............D..P.......................................................I.D 220        230        240        250        260        270        280        290
       |          |          |          |          |          |          |          |
1. MLVDSIGSWSRNILRTQESECVCINGTCTVMTDGSASGRADTRILFIREGKIVHISPLSGSAQHIEECSCYPRYPNVRCVCR
2. ..............Q.........................................................D.
3. ..............Q.........................................................D.
4. ..............Q.........................................................D.

300        310        320        330        340        350        360        370
       |          |          |          |          |          |          |          |
1. VCRDNWKGSNRPVIDINMADYSIDSSYVCSGLVGDTPRNDDSSSSSNCRDPNNERGNPGVKGWAFDNENDVWMGRTISKDLRS
2. ...................S.....................................................S
3. ...................S.....................................................S
4. ...................S.....................................................S 380        390        400        410        420        430        440        450
       |          |          |          |          |          |          |          |
1. LRSGYETFKVIGGWTTANSKLQVNRQVIVDNNNWSGYSGIFSVEGKSCVNRCFYVELIRGGPQETRVWWTSNSIVVFCGTSGT
2. .S.....................................................R.............A.
3. .S.....................................................R.............A.
4. .S.....................................................R.............A.

460
                |
1. SCVNRCFYVELIRGGPQETRVWWTSNSIVVFCGTSGTYGTGSWPDGANINFMPI  (SEQ ID NO.12)
2. ........................R.............A..............  (SEQ ID NO.33)
3. ........................R.............A..............  (SEQ ID NO.34)
4. ........................R.............A..............  (SEQ ID NO.35)
```

Figure 2

[Fig. 4]
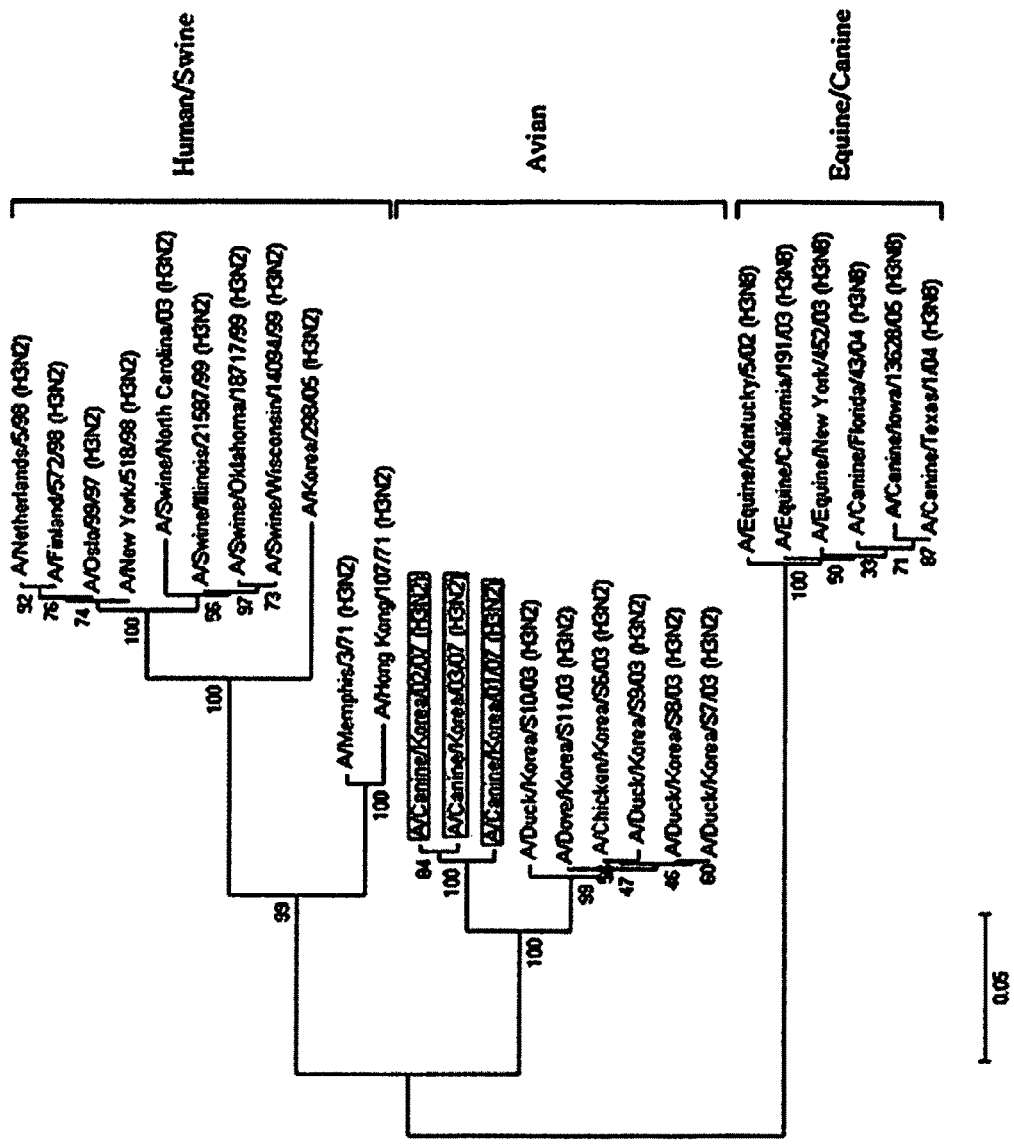

[Fig. 5]
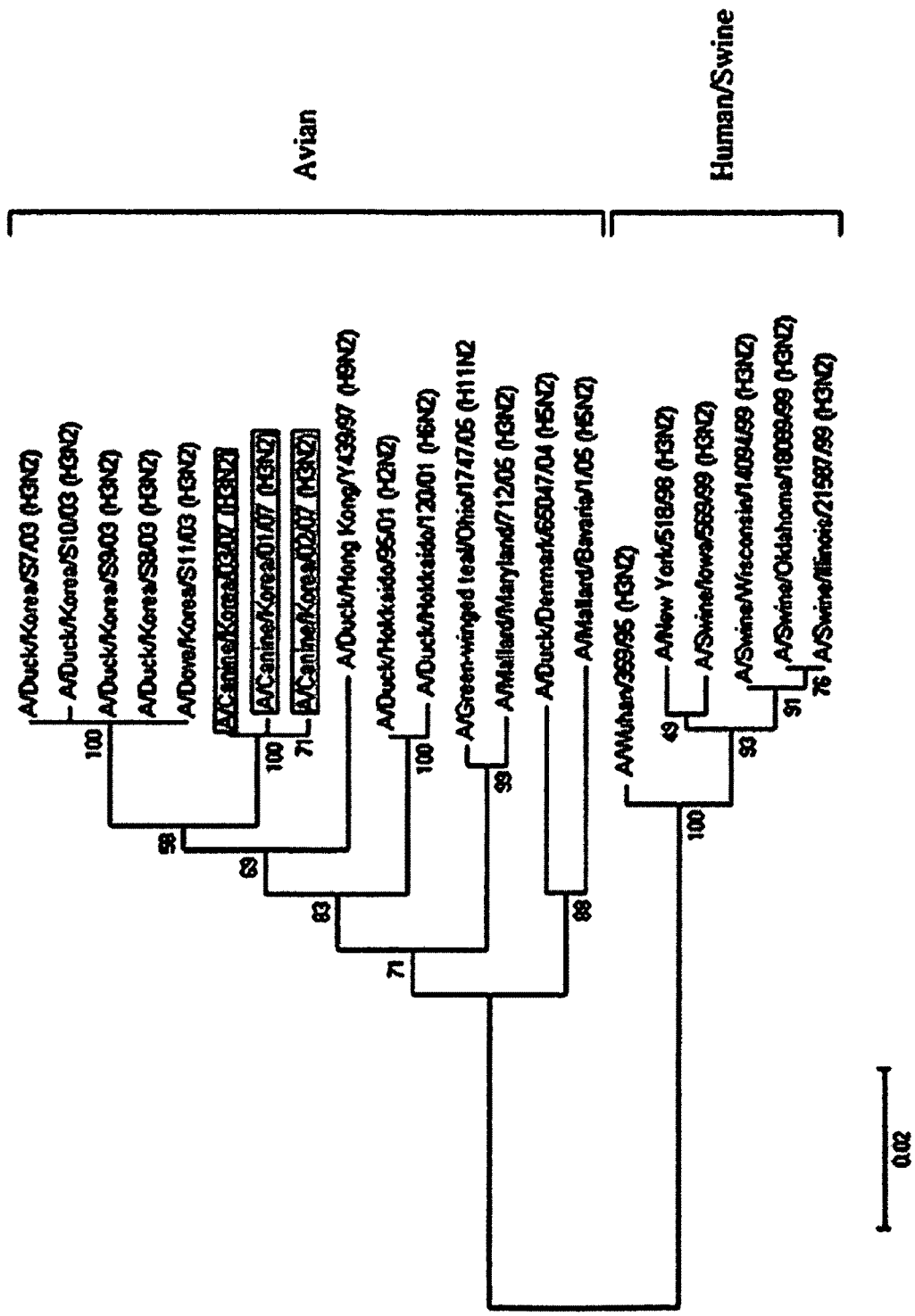

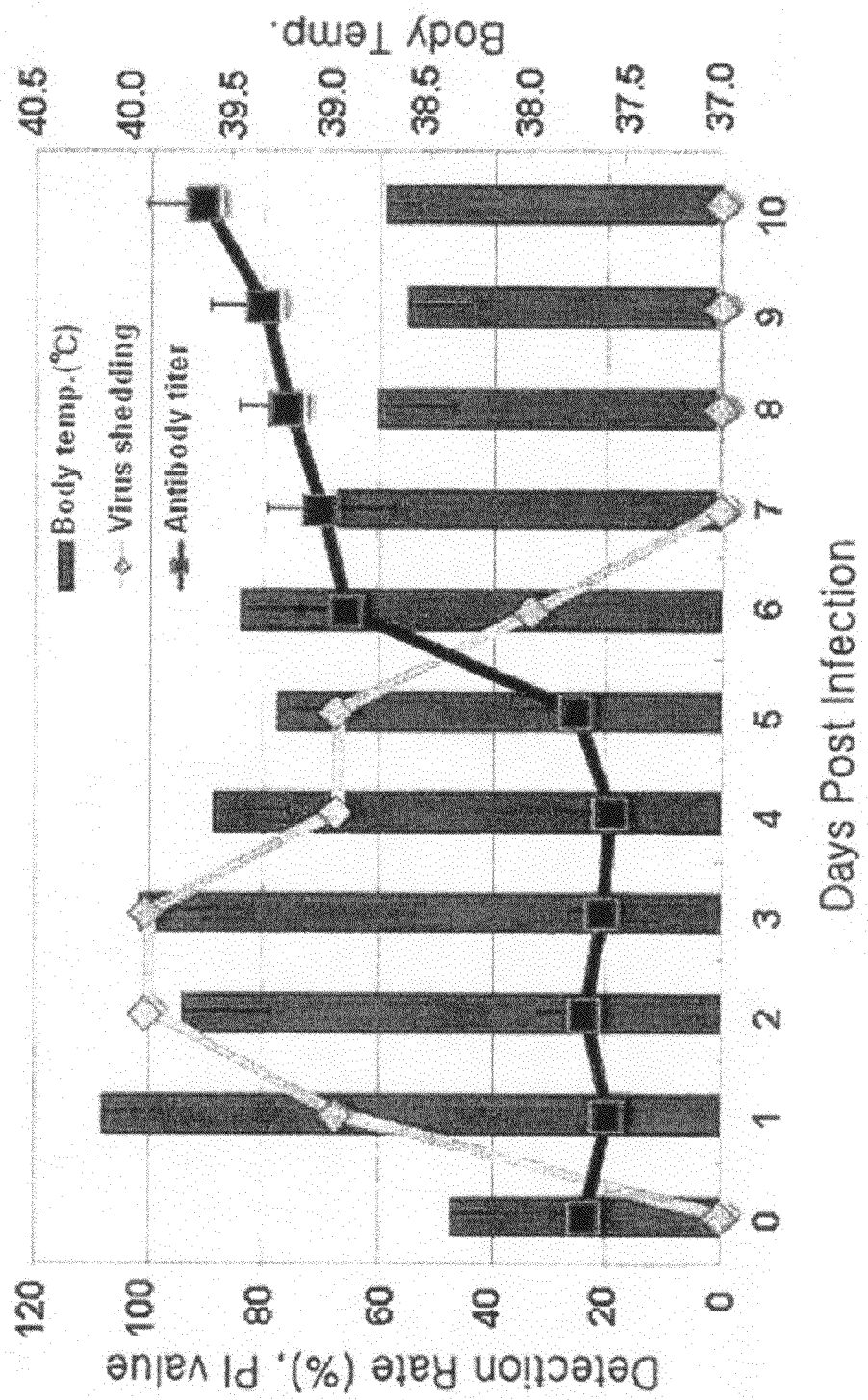
[Fig. 6]

[Fig. 7]
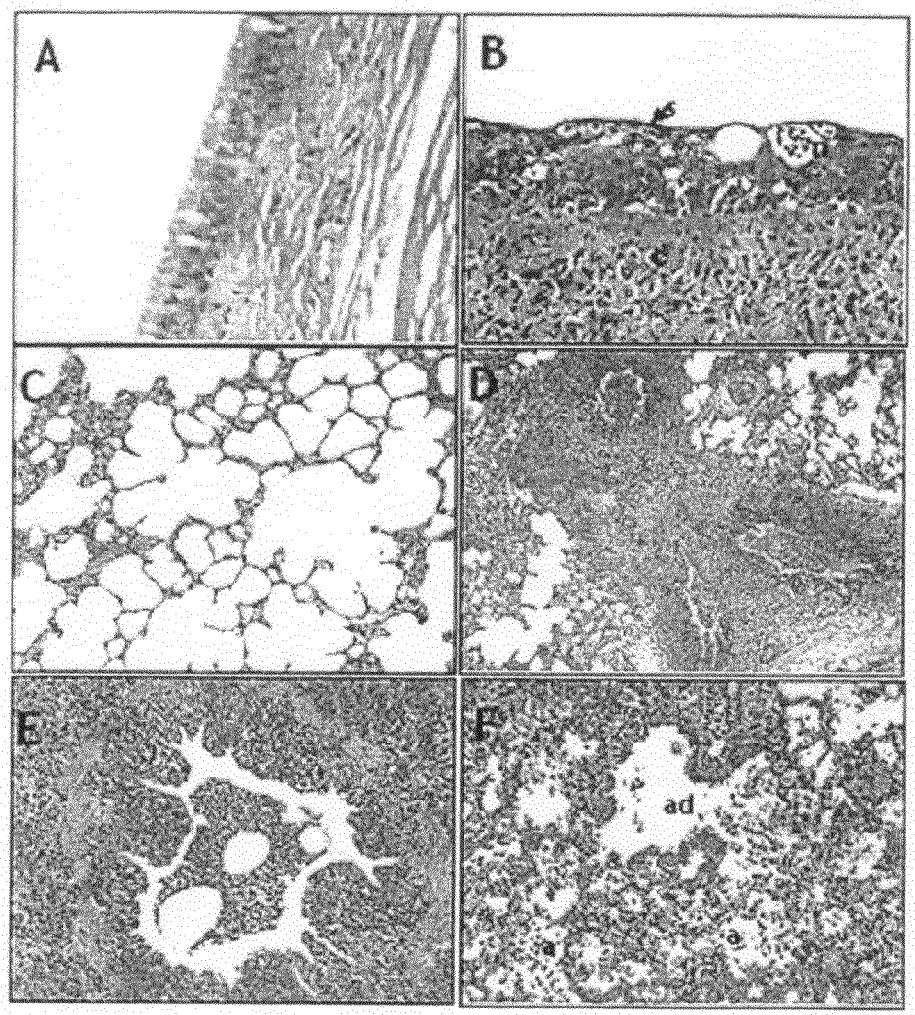

US 8,246,962 B2

CANINE INFLUENZA VIRUS AND VACCINE THEREFORE

This application is U.S. National Phase of International Application PCT/KR2007/005789, filed Nov. 16, 2007 designating the U.S., which claims priority to Korean Patent Application No. 10-2007-0109535, filed Oct. 30, 2007. The International Application has not been published as of the filing date.

TECHNICAL FIELD

The present invention relates to novel influenza viruses A/Canine/Korea/01/07 (H3N2), A/Canine/Korea/02/07 (H3N2) and A/Canine/Korea/03/07 (H3N2), a vaccine composition comprising at least one of the viruses as an active ingredient, a method for preventing or treating diseases resulting from influenza virus infection, and an assay kit for detecting the viruses.

BACKGROUND ART

Influenza, caused by Influenza A virus of the family Orthomyxoviridae, is the most economically important disease in humans, pigs, horses, and fowls.

Influenza A viruses are further classified based on the characteristics of two surface proteins known as hemagglutinin (H) and neuraminidase (N). Influenza A virus is expressed as a combination of the H (hemagglutinin) subtype and N (neuraminidase) type one (e.g., H9N2). There are 16 different H subtypes and 9 N subtypes, resulting in a total of 144 different possible combinations of H and N subtypes of influenza A viruses.

Influenza is a zoonosis. The type A viruses are the most virulent human pathogens among the three influenza types, and cause the most severe disease. In addition, they are highly apt to mutate and can be readily transmitted from one species to another, causing pandemics. Accordingly, the breakout of pandemic influenza is emerging as a great problem to be solved. Furthermore, there are several reports that influenza viruses are infecting new species that have heretofore been known to be resistant to virus infection.

Canine influenza refers to new varieties of Influenza virus A that cause influenza in canines. Because of the lack of previous exposure to this virus, dogs have no natural immunity to this virus. Therefore, all species and ages are susceptible to this virus. Dogs with canine influenza may suffer from acute pneumonia, showing the symptoms of a severe cough, a high fever and rhinorrhea.

A highly contagious influenza virus was found to have been the cause of Greyhound race dog fatalities from a respiratory illness at a Florida racetrack in 2004. Then, as outbreaks thereof were reported in Texas, Alabama, Arkansas and other states in the U.S.A., canine influenza was regarded as a new epidemic in dogs. An epidemiological survey showed the virus, isolated from a dog with canine influenza, was almost identical to the equine influenza virus H3N8, indicating the creation of canine influenza as a result of transmission from horses to dogs. There are reports of the equine influenza virus H3N8 causing hemorrhagic pneumonia in racing dogs and of isolation of the human influenza virus H3N8 from dogs. However, sufficient serological and virological evidence must be found for canine influenza.

In addition, there have been reported cases of the outbreak of avian influenza in canines. It is inferred that the epidemiological mechanism of the transmission of influenza from birds to dogs has two routes: one is by feeding dogs with uncooked birds carrying influenza, such as ducks, chickens, etc.; and the other main way that the influenza virus is spread is from infected dogs to normal dogs in respiratory droplets of coughs and sneezes. As such, it is inferred that canine influenza is established after infected dogs are exposed to new environments and brought into contact with normal dogs. It is important to prevent canine influenza because canine influenza viruses may cause secondary infection with various mortalities. There is no vaccine available for dogs at this time.

DISCLOSURE

Technical Problem

Leading to the present invention, intensive and thorough research into the production of the influenza virus in canines, conducted by the present inventors on the above-mentioned background, resulted in the finding that influenza viruses from some dogs in Korea were A serotype variants, which are different from previous influenza viruses and, although belonging to an avian cluster, showed interspecies transmission among birds and dogs through virological, serological, pathological and phylogenetic analysis. Further, a highly stable vaccine against these viruses has been successfully developed.

Technical Solution

It is an object of the present invention to provide a novel H3N2 serotype canine influenza virus.

It is another object of the present invention to provide a nucleotide sequence encoding a protein constituent of the influenza virus.

It is a further object of the present invention to provide a vaccine composition against the novel virus.

It is still a further object of the present invention to provide an assay kit for detecting H3N2 serotype influenza viruses, comprising the virus of the present invention or an antigenic determinant thereof.

DESCRIPTION OF DRAWINGS

FIG. 1 shows the entire amino acid sequence encoded by an NA gene of A/Canine/Korea/01/07 (H3N2) influenza virus in comparison with those of A/Dove/Korea/S11/03 (H3N2), A/Duck/Korea/S7/03 (H3N2) and A/Chicken/Korea/S6/03 (H3N2) influenza viruses.

FIG. 2 shows the entire amino acid sequence encoded by an HA gene of A/Equine/Jilin/1/1989 (H3N8) influenza virus in comparison with those of A/Canine/Korea/01/07 (H3N2), A/Dove/Korea/S11/03 (H3N2), A/Duck/Korea/S7/03 (H3N2) and A/Chicken/Korea/S6/03 (H3N2) influenza viruses.

FIG. 4 shows a phylogenetic tree for HA gene, rooted with A/Canine/Korea/01/07 (H3N2) influenza virus.

FIG. 5 shows a phylogenetic tree for NA gene, rooted with A/Canine/Korea/01/07 (H3N2) influenza virus.

FIG. 6 is a graph showing changes in body temperature, antibody titer and viral progeny production over one week in animals immunized with A/Canine/Korea/01/07 (H3N2) influenza and animals not immunized therewith.

FIG. 7 shows histopathological lesions in the organs and lungs of animals immunized with A/Canine/Korea/01/07 (H3N2) influenza virus (immunized group B, D and F) and animals not immunized therewith (control, A and C): (A) the pseudostratified columnar epithelium lining in a normal organ of the control group 9 days after aggressive inoculation (400-fold magnification); (B) necrotic organ (n), squamous metaplasia (s), and epithelial hyperplasia and chronic inflammation on connective tissue (C) in the immunized group 9 days after aggressive inoculation (400-fold magnification); (C) normal alveoli of the control group 3 days after aggressive inoculation (200-fold magnification); (D) severe diffuse necrotizing bronchitis and purulent bronchiolitis in the bronchial lumen of the immunized group 3 days after aggressive group (100-fold magnification); (E) severe necrotizing bronchiolitis in the immunized group 6 days after aggressive inoculation (filled with separated necrotizing cells and neutrophils, and mild or moderate chronic inflammation observed around the bronchiole (200-fold magnification); (F) severe necrotizing alveolitis in the immunized group 9 days after aggressive inoculation (necrotizing cell infiltration in the alveolar duct (ad) and alveolus (a) (200-fold magnification) H&E stained).

Best Mode

Figure 3:
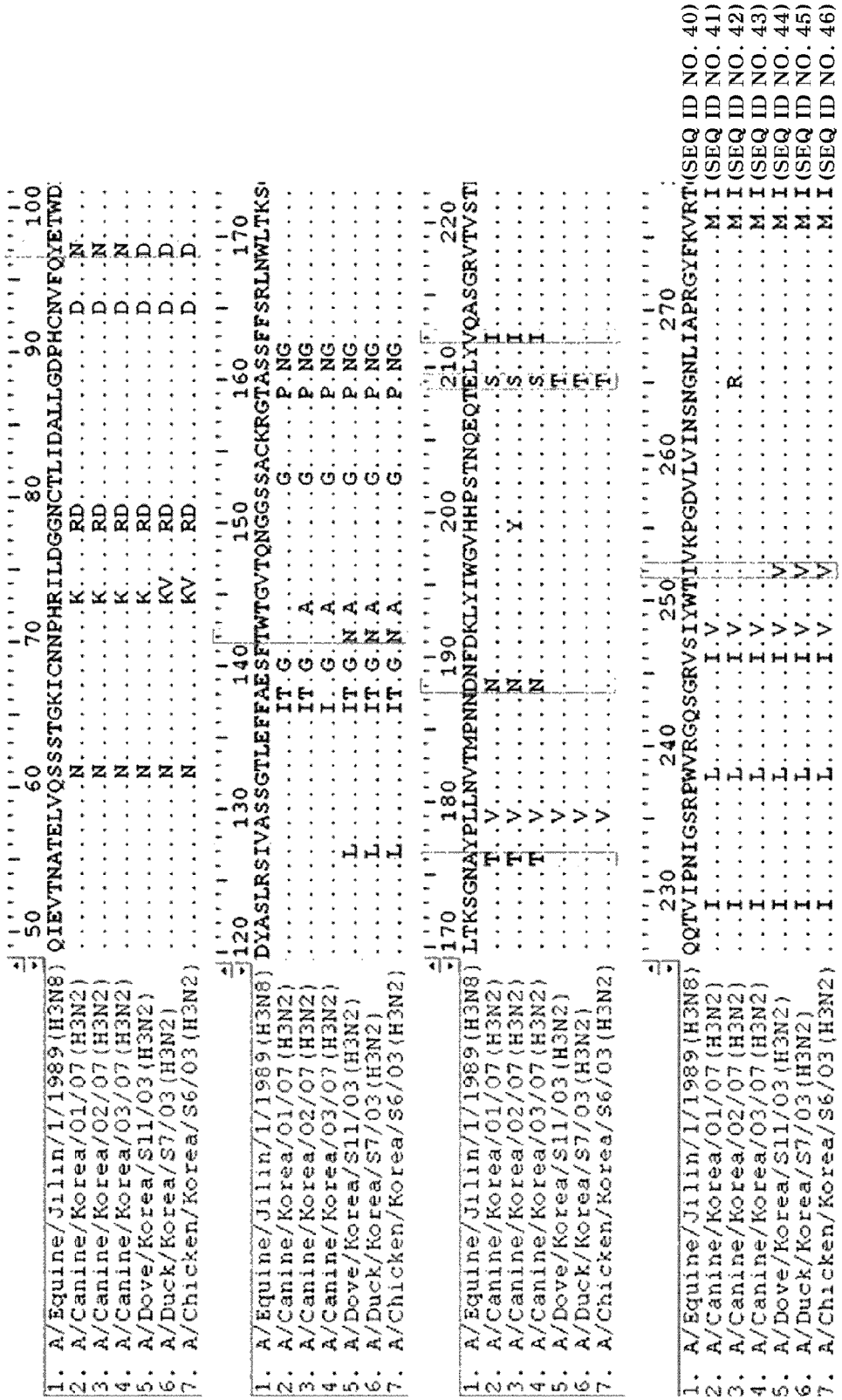
FIG. 3 shows a partial amino acid sequence encoded by an HA gene of A/Equine/Jilin/1/1989 (H3N8) influenza virus in comparison with those of A/Canine/Korea/01/07 (H3N2), A/Canine/Korea/02/07 (H3N2), A/Canine/Korea/03/07 (H3N2), A/Dove/Korea/S11/03 (H3N2), A/Duck/Korea/S7/03 (H3N2) and A/Chicken/Korea/S6/03 (H3N2) influenza viruses.

In accordance with an aspect thereof, the present invention pertains to novel H3N2 serotype canine influenza viruses.

The novel H3N2 serotype canine influenza viruses according to the present invention have a hemagglutinin (HA) protein represented by the amino acid sequence of SEQ ID NO. 10 or an amino acid sequence sharing 95% or higher homology therewith.

Figure 2:
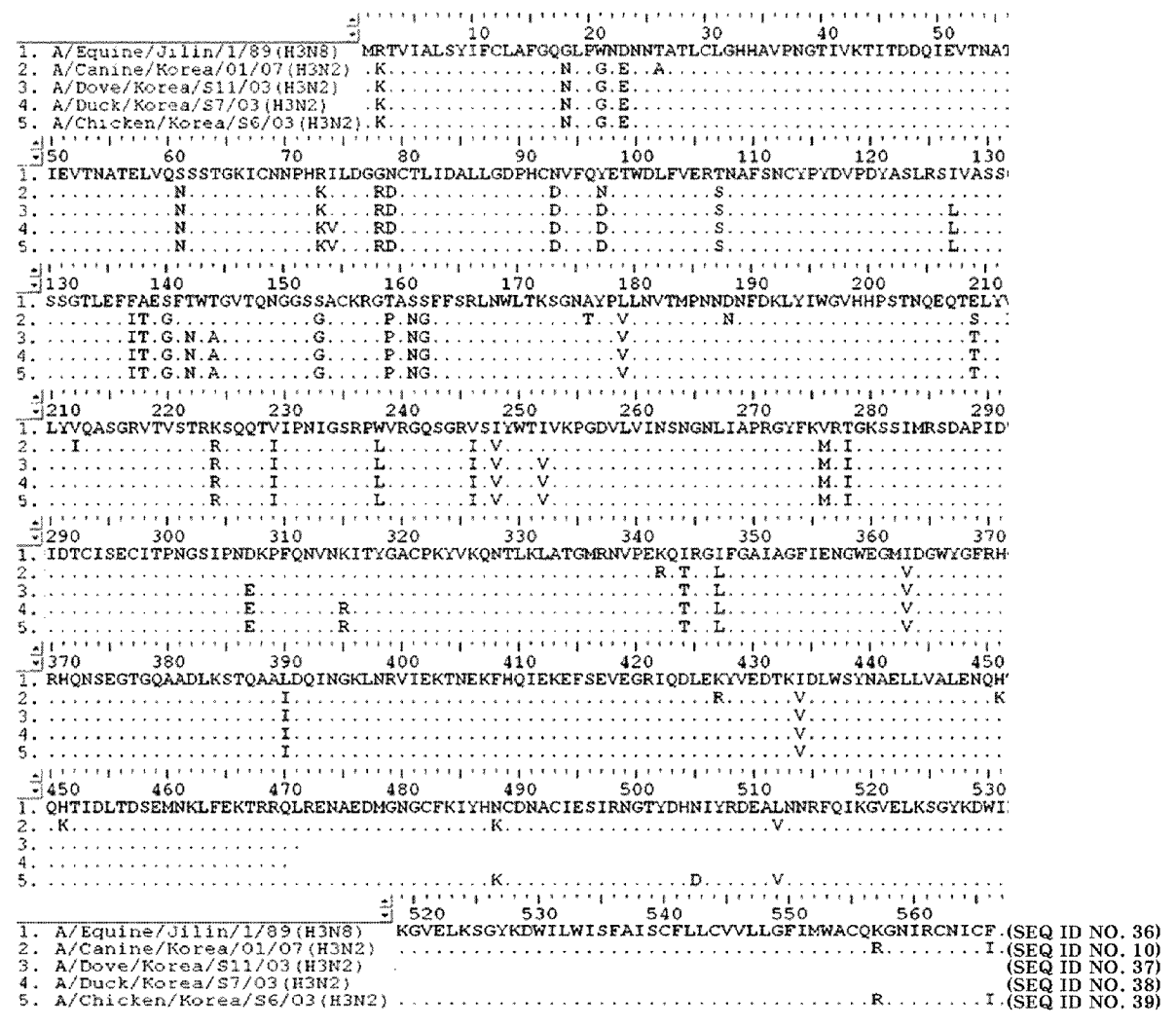

When compared to the previously known equine influenza virus H3N8, the canine influenza virus of the present invention was found to have a very characteristic change in amino acid sequence, as analyzed for the entire neuraminidase (NA) amino acid sequence (FIG. 1) and the entire hemagglutinin (HA) amino acid sequence (FIG. 2). Particularly, the HA amino acid sequences of A/Canine/Korea/01/07 (H3N2), A/Canine/Korea/02/07 (H3N2) and A/Canine/Korea/03/07 (H3N2) are characteristically altered to have N (Asparagine) at position 27, I (Isoleucine) at position 127, T (Threonine) at position 142, T (Threonine) at position 176, N (Asparagine) at position 188, S (Serine) at position 209, I (Isoleucine) at position 212 and I (Isoleucine) at position 252 (FIG. 3). The amino acid sequence sharing at least 95% homology with the amino acid sequence of SEQ ID NO. 10 contains the same amino acid residue as the amino acid sequence of SEQ ID NO. 10 at least one of positions 97, 127, 142, 176, 188, 209, 212 and 252.

Also, the novel H3N2 serotype canine influenza viruses according to the present invention have a neuraminidase (NA) protein, represented by the amino acid sequence of SEQ ID NO. 12, or an amino acid sequence sharing 95% or higher homology therewith.

In addition, the novel canine influenza viruses in accordance with the present invention may further comprise a protein selected from among a non-structural protein (NS), encoded by the nucleotide sequence of SEQ ID NO. 3, a matrix protein (M) encoded by the nucleotide sequence of SEQ ID NO. 4, a nucleoprotein (NP) encoded by the nucleotide sequence of SEQ ID NO. 5, a polymerase (PA) encoded by the nucleotide sequence of SEQ ID NO. 6, a polymerase protein 2 (PB2) encoded by the nucleotide sequence of SEQ ID NO. 7, a polymerase protein 1 (PB1) encoded by the nucleotide sequence of SEQ ID NO. 8, and combinations thereof.

As used for hemagglutinin or neuraminidase herein, the term "homology" is intended to refer to similarity to a wild-type amino acid sequence. The hemagglutinin and the neuraminidase, expressed in the influenza viruses of the present invention, shares 90% or higher, preferably 95% or higher, more preferably 98% or higher, and most preferably 99% or higher homology with the amino acid sequences of SEQ ID NOS. 10 and 12, respectively. In general, a protein homologue has the same active site as the prototype thereof. Homology comparison between amino acid sequences can be conducted using the naked eye or using software. Homology between two or more amino acid sequences can be calculated and expressed as percentages using commercially available software.

The canine influenza viruses of the present invention comprise A/Canine/Korea/01/07 (H3N2), A/Canine/Korea/02/07 (H3N2) and A/Canine/Korea/03/07 (H3N2).

The proteins of the A/Canine/Korea/01/07 (H3N2) influenza virus show 95.5-98.9% homology with those of the avian influenza virus. For example, the A/Canine/Korea/01/07 (H3N2) influenza virus of the present invention shares the highest homology with A/Dove/Korea/S11/03 (H3N2) with regard to HA (Hemagglutinin) and NA (Neuraminidase) genes and with A/Chicken/Nanchang/7-010/2000 (H3N6) with regard to an NS (non-structural) gene. As for genes of PB1 (polymerase basic protein 1), PB2, PA (polymerase), NP (nucleoprotein) and M (matrix), they showed high homologies with avian influenza viruses found in Hong Kong, Japan, and China. The A/Canine/Korea/01/07 (H3N2) influenza virus was deposited at Korean Collection for Type Cultures (KCTC) of Korean Research Institute of Bioscience and Biotechnology, located in 52 Oun-dong, Yusong-Ku, Daejeon, South Korea 305-333 on Sep. 19, 2007, with accession number KCTC 11205BP.

A/Canine/Korea/01/07 (H3N2) influenza virus has a hemagglutinin (HA) gene comprising the nucleotide sequence of SEQ ID NO. 1 and a neuraminidase (NA) gene comprising the nucleotide sequence of SEQ ID NO. 2. The entire nucleotide sequence of HA is given, along with the entire amino acid sequence thereof, in SEQ ID NO. 9, while the entire nucleotide sequence of NA is given, along with the entire amino acid sequence thereof, in SEQ ID NO. 11. In addition, the nucleotide sequence of SEQ ID NO. 3 is contained in the NS gene, the nucleotide of SEQ ID NO. 4 is contained in the M gene, the nucleotide sequence of SEQ ID NO. 5 is contained in the NP gene, the nucleotide sequence of SEQ ID NO. 6 is contained in the PA gene, the nucleotide sequence of SEQ ID NO. 7 is contained in the PB2 gene, and the nucleotide sequence of SEQ ID NO. 8 is contained in the PB1 gene.

The A/Canine/Korea/02/07 (H3N2) influenza virus of the present invention has an HA gene comprising the nucleotide sequence of SEQ ID NO. 13 and an NA gene comprising the nucleotide sequence of SEQ ID NO. 14. This virus was found to be substantially the same as the A/Canine/Korea/01/07 (H3N2) influenza, as the HA and NA nucleotide sequences and amino acid sequences were analyzed to share 98% homology between the two viruses. The A/Canine/Korea/02/07 (H3N2) influenza virus was deposited in Korean Collection for Type Cultures (KCTC) of Korea Research Institute of Bioscience and Biotechnology, located in 52 Oun-dong, Yusong-Ku, Daejeon, South Korea 305-333 on Sep. 19, 2007, with accession number KCTC 11206BP.

The A/Canine/Korea/03/07 (H3N2) influenza virus has an HA gene comprising the nucleotide sequence of SEQ ID NO. 1 and an NA gene comprising the nucleotide sequence of SEQ ID NO. 16. This virus was identified to be substantially the same as the A/Canine/Korea/02/07 (H3N2) influenza virus and the A/Canine/Korea/03/07 (H3N2) influenza virus, as the HA and NA nucleotide sequences and amino acid sequences were analyzed to share 99% homology between the A/Canine/Korea/03/07 (H3N2) influenza virus and the A/Canine/Korea/01/07 (H3N2) influenza virus and 98% homology between the A/Canine/Korea/03/07 (H3N2) influenza virus and the A/Canine/Korea/02/07 (H3N2). The A/Canine/Korea/03/07 (H3N2) influenza virus was deposited in Korean Collection for Type Cultures (KCTC) of Korea Research Institute of Bioscience and Biotechnology, located in 52 Oundong, Yusong-Ku, Daejeon, South Korea 305-333 on Sep. 19, 2007, with accession number KCTC 11207BP.

The canine influenza viruses according to the present invention, isolated from the nasal cavity of Korean dogs, have the phylogenetic relationship shown in the phylogenetic diagrams of FIGS. 4 and 5. The phylogenetic trees of FIGS. 4 and 5, both based on the A/Canine/Korea/01/07 (H3N2) influenza virus, were constructed for the HA gene and the NA gene. As seen in these phylogenetic trees of the HA and NA genes, the influenza viruses of the present invention, along with avian influenza viruses, form a cluster which is different from the cluster to which the H3N8 viruses isolated from horses and dogs belong.

When used to infect dogs, the canine influenza viruses according to the present invention showed pathogenicity, causing fever and pneumonia, and thus are epidemic viruses in dogs in Korea. When administered with vaccines against the canine influenza viruses of the present invention, dogs were, for the most part, found to have immunity to the viruses and to suppress the propagation and generation of viruses therethrough.

In accordance with another aspect thereof, the present invention pertains to a gene encoding a hemagglutinin (HA) protein which has the amino acid sequence of SEQ ID NO. 10 or an amino acid sequence sharing 95% or higher homology therewith. Preferably, the gene has the nucleotide sequence of SEQ ID NO. 9.

Also, the present invention pertains to a gene encoding a neuraminidase (NA) protein which has the amino acid sequence of SEQ ID NO. 12 or an amino acid sequence sharing 95% or higher homology therewith. Preferably, the gene has the nucleotide sequence of SEQ ID NO. 11.

In accordance with a further aspect thereof, the present invention pertains to a vaccine composition which can provide immunity to canine influenza viruses.

Preferably, the vaccine composition of the present invention comprises canine influenza virus or an antigen thereof as an active ingredient. The canine influenza virus for use in the vaccine composition is selected from among A/Canine/Korea/01/07 (H3N2), A/Canine/Korea/02/07 (H3N2), A/Canine/Korea/03/07 (H3N2) and combinations thereof.

The antigen useful in the present invention refers to an antigenic part of the constituents of the virus, which causes an immune response, and may comprise a hemagglutinin (HA) protein having an amino acid sequence sharing 90% or higher homology, and preferably 95% or higher, with the amino acid sequence of SEQ ID NO. 10 or a fragment thereof. The amino acid sequence sharing at least 95% homology with the amino acid sequence of SEQ ID NO. 10 contains the same amino acid residue at least one of positions 97, 127, 142, 176, 188, 209, 212 and 252 as in the amino acid sequence of SEQ ID NO. 10.

Alternatively, the antigen may comprise a neuraminidase (NA) protein having an amino acid sequence sharing 95% or higher homology with the amino acid sequence of SEQ ID NO. 12, or a fragment thereof.

The vaccine according to the present invention may include an attenuated live or killed vaccine, a subunit vaccine, a synthetic vaccine, and a genetically engineered vaccine, with preference for a live vaccine due to the ability thereof to induce an effective immune response.

As used herein, the term "live vaccine" refers to a vaccine prepared from a virus that has been attenuated but can still replicate the cells of the host organism. The term "attenuation", as used herein, is intended to mean artificial reduction in the toxicity of pathogens by mutating a gene involved in the essential metabolism of the pathogen in such a manner that it loses pathogenicity, but retains antigenicity. Generally, attenuation is achieved through UV radiation, chemical treatment, or in vitro sequential high-order subculture. An explicit genetic alteration, such as the deletion of a specific nucleotide in a sequence known to provide toxicity or the insertion of a nucleotide into a viral genome, may also result in attenuation.

As used herein, the term "killed vaccine", also called an inactivated vaccine, refers to a suspension of killed virus used as an antigen to produce immunity. Examples of killed vaccines include whole-virus vaccines and split vaccines. Killed vaccine can be easily produced using known methods. For example, a whole-virus vaccine can be obtained by treating a virus with formalin. Split vaccines are prepared from virus envelopes after treatment with ether.

The term "subunit vaccine" refers to a vaccine composed of a purified antigenic determinant that is separated from the virulent organism by extraction. It is less likely to cause adverse reactions than the whole-virus vaccine. For example, an HA protein and/or an NA protein, extracted from the canine influenza virus, may be used to prepare a subunit vaccine.

By the term "synthetic vaccine" is meant a vaccine consisting mainly of chemically synthetic or genetically engineered antigens, antigenic determinants or peptides. For example, the HA protein and/or the NA protein of the canine influenza virus may be synthesized for use as a vaccine.

A genetically engineered vaccine may be free of a specific gene which is responsible for pathogenicity or may contain a modified gene.

In addition, the influenza vaccine of the present invention may be used in combination with other inactivated organisms or antigens to prepare a mixed or complex vaccine against various diseases including influenza. The term "mixed vaccine", as used herein, is intended to refer to a vaccine prepared from a viral mixture of the canine influenza virus of the present invention and at least one different virus. The term "complex vaccine" means a vaccine prepared from a virus and bacteria. For example, the canine influenza viruses of the present invention may be mixed or combined with canine parainfluenza virus, canine distemper virus, canine adenovirus, and/or Bordetella bronchiseptica.

The canine influenza virus vaccine according to the present invention may be prepared using a method comprising: (a) injecting the canine influenza virus of the present invention into an embryonated egg and proliferating the virus therein; (b) treating a chorioallantoic fluid from the embryonated egg with formalin, BPL (betapropiolactone) or BEI (binary ethyleneimine); and harvesting the inactivated virus from the chemically treated chorioallantoic fluid.

In step (a), the canine influenza virus is injected into an embryonated egg 9-11 days old and incubated at 30 to 40° C. for 24 to 72 hours. In step (b), a chorioallantoic fluid is obtained from the incubated egg using a conventional method, treated with 0.005-0.2 (v/w) % of formalin, BEI or BPL and incubated at a low temperature to inactivate the virus. In step (c), the inactivated virus was harvested from the chorioallantoic fluid treated with formalin, BEI or BPL by centrifugation or filtration. Then, the virus is adsorbed onto aluminum hydroxide gel. This method may comprise well-known techniques, or may be modified into more readily practicable versions.

Also, the vaccine composition of the present invention may further comprise a medium, an adjuvant, and/or an excipient. Physiological saline or distilled water may be used as a medium. Examples of the adjuvant useful in the vaccine composition include a Freund's incomplete or complete adjuvant, aluminum hydroxide gel, vegetable or mineral oil, etc. Examples of the excipient include aluminum phosphate, aluminum hydroxide, and aluminum potassium sulfate, but are not limited thereto. In practice, all materials known for use in vaccine preparation to those skilled in the art may be applicable to the vaccine composition of the present invention.

Preferably, the vaccine composition of the present invention may comprise the canine influenza virus in an amount of $2^5$ HAU (hemagglutination unit). When the canine influenza virus is used in an amount less than $2^5$ HAU, the vaccine cannot induce antibody production effectively. On the other hand, an amount exceeding $2^5$ HAU may be uneconomical.

The vaccine composition according to the present invention may be prepared into oral dosage forms or non-oral dosage forms. Preferable are non-oral dosage forms which can be administered through intradermal, intramuscular, intraperitoneal, intravenous, subcutaneous, intranasal, or epidural routes.

The vaccine composition according to the present invention is applicable to all subjects that are susceptible to A/Canine/Korea/01/07 (H3N2), A/Canine/Korea/02/07 (H3N2) or A/Canine/Korea/03/07 (H3N2) and act as hosts, including humans, pets, poultry and birds, such as dogs, pigs, chicken, ducks, turkeys, etc.

In accordance with a further aspect thereof, the present invention pertains to a method for the prevention and treatment of influenza virus-related diseases, comprising the administration of the vaccine composition to individuals at risk.

As used herein, the term "influenza virus-related disease" is intended to refer to a disease which results from infection with influenza virus. Examples thereof include paranasal sinusitis, spasmodic asthma, tympanitis, cystic fibrosis, bronchitis, pneumonia, diarrhea, etc. (Pitkaranta and Hayden, 1998. Ann. Med.), but are not limited thereto.

The term "individuals", as used herein, is intended to refer to all vertebrates, including humans, which are already infected with, or can be infected with, influenza viruses. By the administration with the vaccine composition of the present invention, the diseases can be effectively prevented and treated. For example, humans infected with various subtypes or variants of influenza viruses can be treated with the vaccine composition of the present invention. In addition, chickens or pigs may be immunized with the vaccine composition in order to take precautions against influenza. The vaccine composition of the present invention may be administered in combination with conventional therapeutics against influenza virus-related diseases.

As used herein, the term "prevention" means all actions for inhibiting influenza virus infection or delaying influenza outbreak through the administration of the vaccine composition according to the present invention. The term "treatment" means all actions by which symptoms resulting from influenza virus infection are relieved or take a turn for the better through administration with the vaccine composition according to the present invention.

In a pharmaceutically effective amount, the vaccine composition according to the present invention is administered. The term "pharmaceutically effective amount", as used herein, is intended to refer to an amount that is useful to treat influenza virus-related diseases at reasonable ratios of beneficence to danger for medicinal therapy. Dosages of the compound of the present invention depend on the kind and severity of diseases, activity of the drug, sensitivity to the drug, frequency and time period of administration, administration routes, excretion rates, and factors well known in the art including, for example, concurrently used drugs, etc. The vaccine composition of the present invention may be used as a single medicine or in combination with other medicines concurrently or sequentially, and may be administered in single dosages or multiple dosages. Taking into account the elements mentioned above, it is important to determine the dosage that elicits maximum therapeutic effects without undesirable side effects, which is easy for those skilled in the art.

In accordance with a further aspect thereof, the present invention pertains to an assay kit for detecting H3N2 serotype influenza viruses, comprising the influenza virus of the present invention or an antigenic determinant thereof.

Through an antigen-antibody complex reaction, the influenza virus of the present invention or an antigenic determinant thereof is useful in the specific detection of influenza viruses as well as the extermination of influenza viruses in cells infected therewith.

This assay kit comprises tools/reagents generally used in the immunological field as well as the influenza virus of the present invention. Examples of the tools/reagents include suitable carriers, labels producing detectable signals, solubilizers, detergents, buffers, stabilizers, etc., but are not limited thereto. When the labels are enzymes, the kit may further comprise substrates for analyzing enzymatic activity and reaction terminators. Examples of suitable carriers include, but are not limited to, soluble carriers, such as physiologically acceptable buffers well known in the art, e.g., PBS, insoluble carriers, such as polystyrene, polyethylene, polypropylene, polyester, polyacrylonitrile, fluorine resin, crosslinking dextran, polysaccharide, etc., magnetic microparticles, such as metal-coated latex, paper, glass, metal, agarose, and combinations thereof.

As for an assay for the formation of antigen-antibody complexes, examples thereof include immunohistochemical staining, radioimmunoassay (RIA), enzyme-linked immunosorbent assay (ELISA), Western blotting, immunoprecipitation assay, immunodiffusion assay, complement fixation assay, FACS, and protein chip, but are not limited thereto.

Labels for allowing the qualitative or quantitative analysis of the antigen-antibody complex are exemplified by enzymes, fluorescents, ligands, luminescents, microparticles, redox molecules and radioisotopes, but are not limited thereby. Examples of enzymes useful as detectable labels include β-glucuronidase, β-D-glucosidase, β-D-galactosidase, urease, peroxidase, alkaline phosphatase, acetylcholine esterase, glucose oxidase, a combination of hexokinase and GDPase, RNase, a combination of glucose oxidase and luciferase, phosphofructokinase, phosphoenolpyruvate carboxylase, aspartate aminotransferase, phosphoenolpyruvate decarboxylase, and β-lactamase, but are not limited thereto. Illustrative, non-limitative examples of the fluorescents useful in the present invention include fluorescein, isothiocyanate, rhodamine, phycoerytherin, phycocyanin, allophycocynanin, o-phthaldehyde, and fluorescamine. A biotin derivative may be used as the ligand, but does not limit the scope of the present invention. Acridinium ester, luciferin, and luciferase are useful as luminescents, but this list is not intended to limit the scope of the present invention. Illustrative, non-limiting microparticles include colloidal gold, coated latex, etc. As redox molecules useful in the present invention, there are ferrocene, ruthenium complex, viologen, quinone, Ti ion, Cs ion, diimide, 1,4-benzoquinone, hydroquinone, $K_4W(CN)_8$, $[Os(bpy)_3]^{2+}$, $[RU(bpy)_3]^{2+}$, and $[MO(CN)_8]^{4-}$, which are given for illustrative purposes only, but are not intended to limit the scope of the present invention. Examples of radioisotopes useful in the present invention include $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$, but are not limited thereto.

Mode for Invention

A better understanding of the present invention may be obtained through the following examples, which are set forth to illustrate, but are not to be construed as the limit of the present invention.

EXAMPLE 1

Specimen Sampling and Virus Isolation

Specimens were sampled from dogs which were treated in veterinary hospitals located in Kyeonggi-Do, Korea: One Miniature Schnauzer dog five years old suffered from rhinorrhea for three days and sneezing for two days and then recovered from the flu; One Cocker Spaniel dog three years old suffered from fever, cough, rhinorrhea and inappetence and finally died: One Yorkshire terrier dog and two Jindo dogs suffered from severe cough, fever and rhinorrhea and died 2 days after hospitalization.

All of these animals were identified to be infected with influenza virus type A as analyzed by a Rapid Kit, purchased from Anigen, and RT-PCR. Other pathogens were not detected from the dogs.

The specimens (nasal secretions) from the animals were inoculated into 11 day old eggs, after which chorioallantoic fluid was sampled therefrom. The fluid was found to aggregate chicken erythrocytes. The viruses isolated from the animals were serologically identified as an H3N2 serotype. These viruses were named A/Canine/Korea/01/07 (H3N2), A/Canine/Korea/02/07 (H3N2) and A/Canine/Korea/03/07 (H3N2) and deposited in Korean Collection for Type Cultures (KCTC) of Korea Research Institute of Bioscience and Biotechnology, located in 52 Oun-dong, Yusong-Ku, Daejeon, South Korea on Sep. 19, 2007, with Accession Numbers KCTC 11205BP, KCTC 11206BP and KCTC 11207BP, respectively.

EXAMPLE 2

Genetic Characteristics of Isolated Viruses

Genetic characteristics of the viruses isolated in Example 1 were determined through gene analysis. Total influenza virus RNA isolated from the chorioallantoic fluid using Trizol LS was used as a template for RT-PCR using random hexamer primers, followed by PCR using primers shown in Table 1. Primer sequences for amplifying H3, N2, PB1, PB2, PA, NP, M and NS genes were designed using a modified Primer 3 program (Whitehead Institute/MT Center for Genome Research).

cDNA (2 µl) was mixed with a reagent mix {2.5 µl, 10× Taq DNA polymerase buffer, $MgCl_2$ 1.5 mM, dNTPs (2.5 mM/µl) 2.0 µl, each primer (10 pmol) 1 µl, Taq DNA polymerase (Promega, USA) 1 µl)} and the final volume was adjusted to 25 µl with distilled water to prepare a PCR mixture. PCR started by denaturation at 94° C. for 10 min, and was performed with 32 cycles of denaturing at 96° C. for 30 sec, annealing at 53° C. for 30 sec, and extending at 72° C. for 2 min, followed by extension at 72° C. for 10 min. PCR was terminated at 4° C. The PCR product thus obtained was analyzed by electrophoresis on 1.5% agarose gel containing ethidium bromide. The sequence data thus obtained were analyzed with Bioedit software.

TABLE 1

PCR Primer Sequences

| Target Genes | Primer Sequence(5'>3') | PCR Products |
|---|---|---|
| H3 | CARATTGARGTGACHAATGC (SEQ ID NO 15)<br>GGTGCATCTGAYCTCATTA (SEQ ID NO 16) | 720 bp |
| N2 | TGTTCCGTTTCATTTGGGAA (SEQ ID NO 17)<br>CCAACAAGCCCTGAACACAC (SEQ ID NO 18) | 477 bp |
| PB1 | AAAGTGCCAGCACAAAATGC (SEQ ID NO 19)<br>TTCTCACAGATGCTCCTCGC (SEQ ID NO 20) | 764 bp |
| PB2 | TCATGGAGGTCGTTTTTCCA (SEQ ID NO 21)<br>TGAATCAGCCTTCTGGTTGC (SEQ ID NO 22) | 661 bp |
| PA | GAAGTGAGCGCCAAAATTGA (SEQ ID NO 23)<br>CTCTGGCTCATCGCTGTCAT (SEQ ID NO 24) | 477 bp |
| NP | ACGGTCTGCACTCATCCTGA (SEQ ID NO 25)<br>GCCCCTGGAAAGACACATCT (SEQ ID NO 26) | 602 bp |
| M | AACATTCCATGGGCTAAGG (SEQ ID NO 27)<br>CGGCAATAACGAGAGGATCA (SEQ ID NO 28) | 456 bp |
| NS | GACTGGTTCATGCTCATGCC (SEQ ID NO 29)<br>GAGAGAGTGAAGGTCCCCCA (SEQ ID NO 30) | 844 bp |

Eight gene segments from A/Canine/Korea/01/07 (H3N2) were base sequenced and compared with genes of GeneBank (SEQ ID NOS. 1 to 12). The viruses according to the present invention were found to have 95.5 to 98.9% homology to previously known avian influenza viruses (Table 2). Particularly, the viruses according to the present invention shared the highest homology with S11, which was isolated in Korea, in terms of the HA and NA genes, and with a strain isolated from chickens in China in terms of the NS gene. As for PB1, PB2, PA, NP and M genes, high homologies were detected between the viruses of the present invention and avian influenza viruses isolated in Hong Kong, Japan and China. HA and NA genes were found to have 98%-99% homology among the viruses of the present invention, A/Canine/Korea/01/07, A/Canine/Korea/02/07 and A/Canine/Korea/03/07, which indicates that they are substantially the same.

TABLE 2

Comparison for Gene Homology of Canine Influenza Viruses

| Viruses | Gene | Highly Homologous Viruses | Influenza Virus Type of RNA Segment | Homology (%) | Rgst'n Nos. |
|---|---|---|---|---|---|
| A/Canine/ Korea/01/07 | HA | A/Chicken/ Korea/ S6/03(H3N2) | Avian | 96.6 | AY862607 |

TABLE 2-continued

Comparison for Gene Homology of Canine Influenza Viruses

| Viruses | Gene | Highly Homologous Viruses | Influenza Virus Type of RNA Segment | Homology (%) | Rgst'n Nos. |
|---|---|---|---|---|---|
| | NA | A/Dove/Korea/S11/03(H3N2) | Avian | 97.4 | AY862644 |
| | PB1 | A/Duck/Yangzhou/02/2005(H8N4) | Avian | 98.9 | EF061124 |
| | PB2 | A/Duck/Zhejiang/11/2000(H5N1) | Avian | 97.6 | AY585523 |
| | PA | A/Duck/Hokkaido/120/2001(H6N2) | Avian | 95.9 | AB286878 |
| | NP | A/Duck/Hong Kong/Y439/97(H9N2) | Avian | 95.5 | AF156406 |
| | M | A/Duck/Jiang Xi/1850/2005(H5N2) | Avian | 97.5 | EF597295 |
| | NS | A/Chicken/Nanchang/7-010/2000(H3N6) | Avian | 97.5 | AT180648 |

EXAMPLE 3

Phylogeny of Isolated Viruses

The position of A/Canine/Korea/01/07 in a phylogenetic tree was determined using a clustal alignment algorithm and MEGALIGN software (DNASTAR, Madison, Wis.). In a point of view of HA and NA genes, the virus of the present invention was identified as belonging to a cluster different from the cluster of previously isolated H3N8 viruses from horses and dogs, and showed a very close genetic relationship with H3N2 viruses isolated in Korea (FIGS. 4 and 5).

EXAMPLE 4

Assay of Isolated Viruses for Pathogenicity

In order to examine the pathogenicity thereof, A/Canine/Korea/01/07 (H3N2) was inoculated into dogs.

Ten beagles 10 weeks old were divided into a test group of 7 and a control group of 3. The seven beagles in the test group were administered intranasally and orally with the isolated virus (2 ml) having an HA titer of 1:64 ($10^{6.9}$ $EID_{50}$/0.1 ml) while the three beagles in the control group were administered intranasally and orally with pathogen-free PBS (phosphate buffer saline, 2 ml), followed by monitoring clinical symptoms for 7 days. The discharge of virus through excretions and rhinorrhea was monitored using RT-PCR for 10 days starting from the day of inoculation. A serological study was conducted using a competitive ELISA Animal Genetics Inc. Korea) with a recombinant NP (nucleoprotein) serving as an antigen. Serum samples were also analyzed in order to detect antibodies to the recombinant NP, as recommended by OIE. Two beagles of the test group and one beagle of the control group were subjected to euthanasia with 1 ml of xylazine at 3, 6 and 9 days each after the inoculation and autopsied in order to observe pathologic lesions.

From day 2 to day 7 after the inoculation, the beagles were observed to suffer from clinical symptoms including sneezing and rhinorrhea. Rectal temperature was maintained at 39° C. in the beagles of the control group throughout the experiment, but increased to 40.14° C. on average in the beagles of the test group 24 after the inoculation (FIG. 6).

Serological tests were negative for the viruses in all of the experimental dogs before the inoculation, and remained negative in the beagles in the test group during the experiment. ELISA showed a far higher percentage inhibition in the test group than in the control group 6 days after the inoculation, indicating that antibodies were produced. Interestingly, the inoculated beagles were found to have an HI titer of 1:80 8 days after inoculation.

The virus was found in the nasal secretion from the inoculated beagles for 6 days after the inoculation, but was not detected in the excretion. Typically, canine influenza virus started to be discharged from dogs 1 day after infection and peaked with a titer of $10^{6.0}$ $EID_{50}$/0.1 ml 4 days after infection.

It was found that histopathological lesions were limited to the lungs. Histologically, serious necrotic lesions were discovered in the upper respiratory tract (bronchi) and the lower respiratory tract (bronchiole and alveolar). Bronchiolitis and bronchitis, although somewhat different in the extent thereof, occurred in all of the inoculated beagles (FIG. 7).

Consequently, the isolated virus was identified to be pathogenic in dogs, causing an increase in body temperature and pneumonia. In addition, it was found that viruses were discharged for 6 days.

EXAMPLE 5

Vaccine Preparation

The newly isolated canine influenza virus A/Canine/Korea/01/07 (H3N2) was seeded into chorioallantoic membranes of embryonated eggs 10 days old. Three days later, a chorioallantoic fluid was sampled as a virus bulk. To this virus bulk was added 0.2% formalin, followed by incubation at room temperature for 24 hours for inactivation thereof. The virus bulk was determined to be inactivated when no viral progeny were detected after the virus bulk had been re-inoculated into the embryonated eggs. The inactivated virus bulk was concentrated into $2^5$ HAU or higher. This bulk was mixed at a ratio of 7:3 with aluminum hydroxide gel by stirring at 10,000 rpm for 10 min. Following a negative test for viruses, the mixture was used as a vaccine.

EXAMPLE 6

Aggressive Inoculation Following Vaccination

The prepared vaccine was subcutaneously injected at a dose of 0.5 ml into ten beagles, each 10 weeks old, and additionally injected in the same manner three weeks later. Two weeks after the secondary injection, the beagles were aggressively inoculated at a dose of 2 ml through an oral or intranasal route, with the isolated virus A/Canine/Korea/01/07 (H3N2), having an HA titer of 1:64 ($10^{6.9}EID_{50}$/0.1 ml). As a control, three beagles were inoculated with PBS before the aggressive inoculation. The experimental animals were monitored for body temperature, virus production, clinical symptoms and antibody titer during the experiment.

Even after inoculation, the vaccinated beagles exhibited no changes in body, discharged no viral progeny, and showed no clinical symptoms. In contrast, the control was increased in body temperature for one week after the inoculation (Table 3). PCR showed that viral progeny was discharged from all three beagles in the control group, but was not discharged from any of them 6 days after inoculation (Table 4). Also, the control group was observed to suffer from clinical symptoms, including rhinorrhea and cough, such as kennel cough or wet productive cough. As for antibody titer, it started to increase with regard to the ELISA antibody to nucleoprotein and the HI antibody to hemagglutinin over the experimental time period starting 7 days after the aggressive inoculation in the vaccinated beagles (Table 5). However, the control started to increase in the titer of antibodies to nucleoprotein and hemagglutinin starting 7 days after the aggressive inoculation.

Therefore, the vaccinated beagles were found to have a defense against the aggressive inoculation, indicating that the vaccine composition of the present invention is useful as a vaccine against the influenza virus.

TABLE 3

Body Temperature in Vaccinated and Unvaccinated Animals After Aggressive Inoculation (Booster on Day 21, Aggressive Inoculation on Day 35)

| Days After Vaccination | Vaccinated Group | Control (Unvaccinated) |
| --- | --- | --- |
| 0 | 37.8 ± 0.1 | 38.2 ± 0.2 |
| 7 | 37.6 ± 0.2 | 37.8 ± 0.1 |
| 14 | 38.4 ± 0.1 | 38.0 ± 0.2 |
| 21 | 38.2 ± 0.1 | 37.6 ± 0.1 |
| 28 | 38.1 ± 0.2 | 38.3 ± 0.1 |
| 35 | 38.3 ± 0.2 | 37.6 ± 0.1 |
| 36 | 40.2 ± 0.3 | 38.3 ± 0.2 |
| 37 | 40.6 ± 0.1 | 38.0 ± 0.3 |
| 38 | 39.84 ± 0.2 | 38.0 ± 0.2 |
| 39 | 39.3 ± 0.1 | 37.6 ± 0.1 |
| 40 | 38.9 ± 0.2 | 38.3 ± 0.1 |
| 41 | 38.7 ± 0.1 | 37.6 ± 0.1 |
| 42 | 38.6 ± 0.1 | 38.0 ± 0.1 |
| 49 | 38.0 ± 0.1 | 38.0 ± 0.1 |

* No. of PCR positive/No. of PCR Tested

TABLE 4

Virus Discharge from Vaccinated and Unvaccinated Animals After Aggressive Inoculation (Booster on Day 21, Aggressive Inoculation on Day 35)

| Days After Vaccination | Vaccinated Group | Control (Unvaccinated) |
| --- | --- | --- |
| 0 | 0/10* | 0/3 |
| 7 | 0/10 | 0/3 |
| 14 | 0/10 | 0/3 |
| 21 | 0/10 | 0/3 |
| 28 | 0/10 | 0/3 |

TABLE 4-continued

Virus Discharge from Vaccinated and Unvaccinated Animals After Aggressive Inoculation (Booster on Day 21, Aggressive Inoculation on Day 35)

| Days After Vaccination | Vaccinated Group | Control (Unvaccinated) |
| --- | --- | --- |
| 35 | 0/10 | 0/3 |
| 36 | 0/10 | 3/3 |
| 37 | 0/10 | 3/3 |
| 38 | 0/10 | 3/3 |
| 39 | 0/10 | 3/3 |
| 40 | 0/10 | 2/3 |
| 41 | 0/10 | 0/3 |
| 42 | 0/10 | 0/3 |
| 49 | 0/10 | 0/3 |

*PI value positive

TABLE 5

Antibody Titer in Vaccinated and Unvaccinated Animals After Aggressive Inoculation (Booster on Day 21, Aggressive Inoculation on Day 35)

| Days After Vaccination | Vaccinated Group | | Control (Unvaccinated) | |
| --- | --- | --- | --- | --- |
| | ELISA* | HI | ELISA | HI |
| 0 | 14 | <10 | 12 | <10 |
| 7 | 89 | 10 | 20 | <10 |
| 14 | 87 | 40 | 14 | <10 |
| 21 | 96 | 40 | 19 | <10 |
| 28 | 89 | 80 | 26 | <10 |
| 35 | 94 | 80 | 18 | <10 |
| 42 | 92 | 80 | 97 | 80 |
| 49 | 98 | 160 | 92 | 160 |

INDUSTRIAL APPLICABILITY

As described hitherto, the present invention provides novel canine influenza viruses and a vaccine against the same. Capable of inducing effective immunity against the canine influenza virus, the vaccine is useful in the prevention and treatment of influenza virus-related diseases in dogs and individuals secondarily infected from dogs.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An H3N2 serotype influenza virus, comprising:
   a hemagglutinin (HA) protein comprising amino acid sequence of SEQ ID NO. 10 or an amino acid sequence sharing at least 98% homology with the amino acid sequence of SEQ ID NO. 10; and
   a neuraminidase (NA) protein comprising amino acid sequence of SEQ ID NO. 12 or an amino acid sequence sharing at least 98% homology with the amino acid sequence of SEQ ID NO. 12.

2. The H3N2 serotype influenza virus according to claim 1, wherein the amino acid sequence sharing at least 98% homology with the amino acid sequence of SEQ ID NO. 10 contains the same amino acid residue as the amino acid sequence of SEQ ID NO. 10 at least one of positions 97, 127, 142, 176, 188, 209, 212 and 252.

3. The H3N2 serotype influenza virus according to claim 1, having accession number KCTC 11205BP.

4. The H3N2 serotype influenza virus according to claim 1, having accession number KCTC 11206BP.

5. The H3N2 serotype influenza virus according to claim 1, having accession number KCTC 11207BP.

6. An influenza virus vaccine composition, comprising the H3N2 virus of claim 1 acid sequence of SEQ ID NO. 10 or 12—has been deleted and—, wherein the influenza virus is attenuated—inserted therefor.

7. The influenza virus vaccine composition according to claim 6, further comprising aluminum hydroxide gel or oil as an adjuvant.

8. The influenza virus vaccine composition according to claim 6, wherein said vaccine composition further comprises canine parainfluenza virus, canine distemper virus, canine adenovirus or Bordetella bronchiseptica, wherein the viruses and bacteria in the vaccine composition are attenuated.

9. The influenza virus vaccine composition according to claim 6, comprising the influenza virus in an amount of $2^5$ HAU or higher.

10. A method of preventing or treating diseases in canine resulting from influenza virus infection, the method comprising administering the influenza virus vaccine composition of claim 6 to canine in need of such administration.

11. An assay kit for detecting an H3N2 serotype influenza virus, the kit comprising the virus of claim 1.

12. The H3N2 serotype influenza virus according to claim 1, comprising a hemagglutinin (HA) nucleotide comprising the nucleotide sequence of SEQ ID. 9 or a nucleotide sequence sharing at least 98% homology with the nucleotide sequence of SEQ ID NO. 9, and a neuraminidase (NA) nucleotide comprising the nucleotide sequence of SEQ ID. 11 or a nucleotide sequence sharing at least 98% homology with the nucleotide sequence of SEQ ID NO. 11.

13. An influenza virus immunogenic composition, comprising the H3N2 virus of claim 1 or an antigenic determinant thereof, wherein the antigenic determinant is selected from the group consisting of a hemagglutinin (HA) protein comprising the amino acid sequence of SEQ ID NO. 10, a neuraminidase (NA) protein comprising the amino acid sequence of SEQ ID NO. 12, and an amino acid sequence sharing at least 98% homology with the amino acid sequence of SEQ ID NO. 10 or 12.

14. A method of inducing an immune response in canine, the method comprising administering the immunogenic composition of claim 13 to a canine.

* * * * *

SEQUENCE LISTING

<160> NUMBER OF SEQ ID NOS: 32

<210> SEQ ID NO 1
<211> LENGTH: 722
<212> TYPE: DNA
<213> ORGANISM: Artificial Sequence
<220> FEATURE:
<223> OTHER INFORMATION: HA partial gene of A/Canine/Korea/01/07(H3N2)

<400> SEQUENCE: 1

```
cagattgagg tgaccaatgc cactgagcta gtccaaaact cctcaacagg gaaaatatgc      60
aacaatcccc acaagattct tgatgggagg gactgcacac taatagatgc cctactaggg     120
```

```
gacccgcact gtgatgtctt ccaaaatgag acatgggacc tttttgtgga acgaagcaat    180
gcttttagca attgttaccc ttatgatgta ccagactatg catcccttcg atccatagtt    240
gcatcatcag gcacattgga gttcatcact gaaggtttca cttgggcagg agtaactcaa    300
aatagaggaa gcggtgcttg caaaagggga cctgctaatg gtttcttcag tagattgaat    360
tggttaacta agtcaggaaa tacatatcca gtgttgaatg tgactatgcc aaacaataac    420
aatttcgaca aattatacat ttggggagtt catcacccaa gcactaatca agaacaaacc    480
agcctgtata ttcaggcctc aggaagagtc acagtctcta ccaggagaag ccaacagacc    540
ataatcccaa acattggatc tagacccttg gtaaggggcc aatctggcag aataagcgta    600
tattggacaa tagtcaaacc tggagacgta ctggtaataa acagtaatgg aaacctaatc    660
gctcctcgag gctacttcaa aatgcgcatt gggaaaagct caataatgag atcagatgca    720
cc                                                                  722

<210> SEQ ID NO 2
<211> LENGTH: 477
<212> TYPE: DNA
<213> ORGANISM: Artificial Sequence
<220> FEATURE:
<223> OTHER INFORMATION: NA partial gene of A/Canine/Korea/01/07(H3N2)

<400> SEQUENCE: 2
ccaacaagcc ctgaacacac ataactggaa tcgatgctat aatctgccat atttatatct     60
ataacgggcc tattagagcc cttccaattg tctctgcaaa cacatctaac atttggatat    120
cgaggataac aggaacattc ctctatatgt tgagcactcc ctgacaatgg gctaatatgg    180
acaattttcc cctctctgat gaatagtatt ctagtatcag cccttcctga tgcacttcca    240
tcagtcatta ctactgtaca agttccatta atgcaaacgc attctgactc ctgagttctg    300
aggatatttc gagaccatga accaatactg tcaacaagca ttccattata aacgaaacta    360
gcagtcgcat ttctatcatc cccagtgaca caaacatgta accatgcttt cccatcgtga    420
caacttgaac tggaccatgc tatgcacact tgtttggttc ccaaatgaaa cggaaca      477

<210> SEQ ID NO 3
<211> LENGTH: 240
<212> TYPE: DNA
<213> ORGANISM: Artificial Sequence
<220> FEATURE:
<223> OTHER INFORMATION: NS partial gene of A/Canine/Korea/01/07(H3N2)

<400> SEQUENCE: 3
tggaccaggc aataatggat aaaaacatca cattgaaagc aaacttcagt gtgattttg      60 agcgactgga aaccctaata ctacttagag cttttcacaa cgaaggagca attgtgggag    120
aaatttcacc gttaccttct cttccaggac atactgataa ggatgtcaaa aatgcaattg    180
gggtcctcat cggaggactg aatggaatg ataacacagt tcgagtctct gaaactctac     240

<210> SEQ ID NO 4
<211> LENGTH: 406
<212> TYPE: DNA
<213> ORGANISM: Artificial Sequence
<220> FEATURE:
<223> OTHER INFORMATION: M partial gene of A/Canine/Korea/01/07(H3N2)

<400> SEQUENCE: 4
gcacttgcca gttgtatggg tctcatatac aacaggatgg gaacagtgac cacagaagtg     60
gcttttggcc tagtgtgtgc cacctgtgag cagattgctg attcacagca tcggtcccac    120
```

```
aggcagatgg taactaccac caacccacta atcaggcatg aaaacaggat ggtgctagcc      180
agcaccacag ctaaggctat ggagcagatg gctgggtcga gtgagcaggc agcggaagcc      240
atggaggttg ccagtcaggc taggcagatg gtgcaagcaa tgaggacaat tggaactcac      300
cctagctcca gtgccggtct gaaagatgat cttcttgaaa acttgcaggc ctaccagaaa      360
cggatgggag tgcaaatgca gcgatttaag tgatcctccg tttatt                    406

<210> SEQ ID NO 5
<211> LENGTH: 582
<212> TYPE: DNA
<213> ORGANISM: Artificial Sequence
<220> FEATURE:
<223> OTHER INFORMATION: NP partial gene of A/Canine/Korea/01/07(H3N2)

<400> SEQUENCE: 5
tcatcctgag aggatcagtg gcccataagt cctgcttgcc tgcttgtgtg tacggacttg      60
ccgtggccag tggatatgat tttgagagag aagggtactc tctggttgga atagatcctt     120
tccgtctgct tcaaaacagc caggtcttca gtctcattag accaaatgag aatccagcac     180
ataagagtca gttggtgtgg atggcatgcc attctgcagc atttgaggac ctaagagtct     240
caagtttcat cagaggaaca agagtaattc aagaggaca actatccacc agaggagttc      300 aaaattgcttc aaatgagaac atggaaaaaa tagactccag tactcttgaa ctgagaagca     360
gatattgggc tataagaacc aggagtggag ggaacaccaa ccaacagaga gcatctgcag     420
gacaaatcag tgtacagcca actttctcgg tacagagaaa tattcccttc gagcgagcta     480
ccattatggc aacattcaca gggaatactg agggcagaac atctgacatg cggactgaaa     540
tcataagaat gatggaaagt gccaaaccag aagatgtgtc tt                        582

<210> SEQ ID NO 6
<211> LENGTH: 438
<212> TYPE: DNA
<213> ORGANISM: Artificial Sequence
<220> FEATURE:
<223> OTHER INFORMATION: PA partial gene of A/Canine/Korea/01/07(H3N2)

<400> SEQUENCE: 6
cgccaaaatt gaaccatttt tgaagacaac accacgccct ctcagattac ctgatgggcc      60
tccctgcacc caacggtcaa aattcttgct gatggatgct ctgaacctaa gcattgaaga     120
cccgagtcat gaggggagg ggataccgct atacgatgcg atcaaatgca ctgaagacat      180
ttttcggctg gaaagagccc aacataacca aaccacatga gaaaggcata aaccccaatt     240
atctcttggc ttggaaacag gtgctagcag agctccagaa tattgaaaat gaggagaaaa     300
tcccaaagac aaagaatatg aagaaaacaa gccaattaaa atgggtagct tggtgaaaat     360
atggcaccag aaaagtggac ctttgaggat tgcaaggatg ttagcgacct aaaacaatat     420
gacagcgatg agccagag                                                   438

<210> SEQ ID NO 7
<211> LENGTH: 592
<212> TYPE: DNA
<213> ORGANISM: Artificial Sequence
<220> FEATURE:
<223> OTHER INFORMATION: PB2 partial gene of A/Canine/Korea/01/07(H3N2)

<400> SEQUENCE: 7
aattgacaat aacaaagag aagaaggaag agctccaaga ttgtaagatt gctccttta       60 tggtggcata catgttggaa agagaactgg tccgcaaaac caggttccta ccggtagcag    120
```

```
gcggaacaag cagtgtgtac attgaggtat tgcatttgac acaagggacc tgctgggaac      180
agatgtacac tccaggcgga gaagtgagaa atgacgatgt tgaccagagt ttgatcatcg      240
ccgccagaaa cattgttagg agagcaacgg tatcagcgga tccactggca tcactgctgg      300
agatgtgcca cagcacacaa attggtggga taaggatggt ggacatcctt aggcaaaatc      360
caactgagga acaagctgtg gatatatgca aagcagcaat gggtttgagg atcagttcat      420
cctttagctt tggaggcttc acttttcaaaa gaacaagtgg gtcatccgtc aagaaggaag     480
aggaagtgct cacaggaaac ctccaaacat tgaaaataag agtacatgag gggtatgagg      540
aattcacaat agttgggcgg agagcaacag ctatcctaag gaaagcaacc ag              592
```

```
<210> SEQ ID NO 8
<211> LENGTH: 603
<212> TYPE: DNA
<213> ORGANISM: Artificial Sequence
<220> FEATURE:
<223> OTHER INFORMATION: PB1 partial gene of A/Canine/Korea/01/07(H3N2)

<400> SEQUENCE: 8
ggacaacaaa cacagagact ggagcacccc aactcaatcc aattgatgga ccactacccg      60
aggataatga gccaagcgga tatgcacaaa cagattgtgt gttggaagca atggctttcc      120
ttgaagagtc ccacccaggg atctttgaaa actcatgtat tgaaacgatg gaagttgttc      180
agcaaacaag agtggacaaa ttgacccaag gtcgccagac ctatgactgg acattgaata      240
gaaaccagcc ggctgcaact gctttggcca atactataga ggtcttcaga tcgaacggtc      300
taacagccaa tgaatcggga agactaatag atttccttaa ggatgtaatg gaatcaatgg      360
acaaagaaga gatggagata acaacacatt tccagagaaa aagaagagta agggacaaca      420
tgaccaagaa aatggtcaca cagaggacaa tagggaagaa aaagcagagg ctgaacaaga      480
ggagctacgt aataagagca ctgacattga acacaatgac caaggatgca gaaagaggca      540
aattgaagag gcgggcaatt gcaacacccg ggatgcagat cagagggttc gtgtactttg      600
ttg                                                                   603
```

```
<210> SEQ ID NO 9
<211> LENGTH: 1701
<212> TYPE: DNA
<213> ORGANISM: Artificial Sequence
<220> FEATURE:
<223> OTHER INFORMATION: HA full gene of A/Canine/Korea/01/07(H3N2)
<220> FEATURE:
<221> NAME/KEY: CDS
<222> LOCATION: (1)..(1698)
<223> OTHER INFORMATION: HA amino acid of A/Canine/Korea/01/07(H3N2)

<400> SEQUENCE: 9
```

| | | | | | | | | | | | | | | | | |
|---|---|---|---|---|---|---|---|---|---|---|---|---|---|---|---|---|
| atg | aag | acc | gtt | att | gct | tta | agc | tac | att | ttc | tgc | ctg | gct | ttt | ggt | 48 |
| Met | Lys | Thr | Val | Ile | Ala | Leu | Ser | Tyr | Ile | Phe | Cys | Leu | Ala | Phe | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cag | aat | ctt | cca | gga | aat | gaa | aat | aat | gct | gca | aca | cta | tgc | ctg | gga | 96 |
| Gln | Asn | Leu | Pro | Gly | Asn | Glu | Asn | Asn | Ala | Ala | Thr | Leu | Cys | Leu | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| cat | cat | gca | gtg | ccg | aac | ggg | aca | ata | gtg | aaa | act | atc | aca | gac | gat | 144 |
| His | His | Ala | Val | Pro | Asn | Gly | Thr | Ile | Val | Lys | Thr | Ile | Thr | Asp | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| caa | att | gag | gtg | acc | aac | gcc | acc | gag | cta | gtc | caa | aac | tcc | tca | aca | 192 |
| Gln | Ile | Glu | Val | Thr | Asn | Ala | Thr | Glu | Leu | Val | Gln | Asn | Ser | Ser | Thr | |
| 50 | | | | | 55 | | | | | 60 | | | | | | |

| | | | | | | | | | | | |
|---|---|---|---|---|---|---|---|---|---|---|---|
| ggg | aaa | ata | tgc | aac | aat | ccc | cac | aag | att | ctt | gat | ggg | agg | gac | tgc | 240 |

-continued

| | | | | | | | | | | | | | | | | |
|---|---|---|---|---|---|---|---|---|---|---|---|---|---|---|---|---|
|Gly|Lys|Ile|Cys|Asn|Asn|Pro|His|Lys|Ile|Leu|Asp|Gly|Arg|Asp|Cys| |
|65| | | |70| | | |75| | | |80| | | | |

| aca | cta | ata | gat | gcc | cta | cta | ggg | gac | ccg | cac | tgt | gat | gtc | ttc | caa | 288 |
|---|---|---|---|---|---|---|---|---|---|---|---|---|---|---|---|---|
| Thr | Leu | Ile | Asp | Ala | Leu | Leu | Gly | Asp | Pro | His | Cys | Asp | Val | Phe | Gln | |
| | | | | 85 | | | | | 90 | | | | | 95 | | |

| aat | gag | aca | tgg | gac | ctt | ttt | gtg | gaa | cga | agc | aat | gct | ttt | agc | aat | 336 |
|---|---|---|---|---|---|---|---|---|---|---|---|---|---|---|---|---|
| Asn | Glu | Thr | Trp | Asp | Leu | Phe | Val | Glu | Arg | Ser | Asn | Ala | Phe | Ser | Asn | |
| | | | 100 | | | | | 105 | | | | | 110 | | | |

| tgt | tac | cct | tat | gat | gta | cca | gac | tat | gca | tcc | ctt | cga | tcc | ata | gtt | 384 |
|---|---|---|---|---|---|---|---|---|---|---|---|---|---|---|---|---|
| Cys | Tyr | Pro | Tyr | Asp | Val | Pro | Asp | Tyr | Ala | Ser | Leu | Arg | Ser | Ile | Val | |
| | | | 115 | | | | | 120 | | | | | 125 | | | |

| gca | tca | tca | ggc | aca | ttg | gag | ttc | atc | act | gaa | ggt | ttc | act | tgg | aca | 432 |
|---|---|---|---|---|---|---|---|---|---|---|---|---|---|---|---|---|
| Ala | Ser | Ser | Gly | Thr | Leu | Glu | Phe | Ile | Thr | Glu | Gly | Phe | Thr | Trp | Thr | |
| | | 130 | | | | | 135 | | | | | 140 | | | | |

| gga | gta | act | cag | aat | gga | gga | agc | ggt | gct | tgc | aaa | agg | gga | cct | gct | 480 |
|---|---|---|---|---|---|---|---|---|---|---|---|---|---|---|---|---|
| Gly | Val | Thr | Gln | Asn | Gly | Gly | Ser | Gly | Ala | Cys | Lys | Arg | Gly | Pro | Ala | |
| 145 | | | | | 150 | | | | | 155 | | | | | 160 | |

| aat | ggt | ttc | ttc | agt | aga | ttg | aat | tgg | tta | act | aag | tca | gga | aat | aca | 528 |
|---|---|---|---|---|---|---|---|---|---|---|---|---|---|---|---|---|
| Asn | Gly | Phe | Phe | Ser | Arg | Leu | Asn | Trp | Leu | Thr | Lys | Ser | Gly | Asn | Thr | |
| | | | | 165 | | | | | 170 | | | | | 175 | | |

| tat | cca | gtg | ttg | aat | gtg | act | atg | cca | aac | aat | aac | aat | ttc | gac | aaa | 576 |
|---|---|---|---|---|---|---|---|---|---|---|---|---|---|---|---|---|
| Tyr | Pro | Val | Leu | Asn | Val | Thr | Met | Pro | Asn | Asn | Asn | Asn | Phe | Asp | Lys | |
| | | | 180 | | | | | 185 | | | | | 190 | | | |

| tta | tac | att | tgg | gga | gtt | cat | cac | cca | agc | act | aat | caa | gaa | caa | acc | 624 |
|---|---|---|---|---|---|---|---|---|---|---|---|---|---|---|---|---|
| Leu | Tyr | Ile | Trp | Gly | Val | His | His | Pro | Ser | Thr | Asn | Gln | Glu | Gln | Thr | |
| | | | 195 | | | | | 200 | | | | | 205 | | | |

| agc | ctg | tat | att | cag | gcc | tca | gga | aga | gtc | aca | gtc | tct | acc | agg | aga | 672 |
|---|---|---|---|---|---|---|---|---|---|---|---|---|---|---|---|---|
| Ser | Leu | Tyr | Ile | Gln | Ala | Ser | Gly | Arg | Val | Thr | Val | Ser | Thr | Arg | Arg | |
| 210 | | | | | 215 | | | | | 220 | | | | | | |

| agc | caa | cag | acc | ata | atc | cca | aac | att | gga | tct | aga | ccc | ttg | gta | agg | 720 |
|---|---|---|---|---|---|---|---|---|---|---|---|---|---|---|---|---|
| Ser | Gln | Gln | Thr | Ile | Ile | Pro | Asn | Ile | Gly | Ser | Arg | Pro | Leu | Val | Arg | |
| 225 | | | | | 230 | | | | | 235 | | | | | 240 | |

| ggc | caa | tct | ggc | aga | ata | agc | gta | tat | tgg | aca | ata | gtc | aaa | cct | gga | 768 |
|---|---|---|---|---|---|---|---|---|---|---|---|---|---|---|---|---|
| Gly | Gln | Ser | Gly | Arg | Ile | Ser | Val | Tyr | Trp | Thr | Ile | Val | Lys | Pro | Gly | |
| | | | | 245 | | | | | 250 | | | | | 255 | | |

| gac | gta | ctg | gta | ata | aac | agt | aat | gga | aac | cta | atc | gct | cct | cga | ggc | 816 |
|---|---|---|---|---|---|---|---|---|---|---|---|---|---|---|---|---|
| Asp | Val | Leu | Val | Ile | Asn | Ser | Asn | Gly | Asn | Leu | Ile | Ala | Pro | Arg | Gly | |
| | | | 260 | | | | | 265 | | | | | 270 | | | |

| tac | ttc | aaa | atg | cgc | att | ggg | aaa | agc | tca | ata | atg | aga | tca | gat | gca | 864 |
|---|---|---|---|---|---|---|---|---|---|---|---|---|---|---|---|---|
| Tyr | Phe | Lys | Met | Arg | Ile | Gly | Lys | Ser | Ser | Ile | Met | Arg | Ser | Asp | Ala | |
| | | | 275 | | | | | 280 | | | | | 285 | | | |

| cct | att | gac | acc | tgc | att | tcc | gaa | tgt | atc | act | ccg | aac | ggg | agc | atc | 912 |
|---|---|---|---|---|---|---|---|---|---|---|---|---|---|---|---|---|
| Pro | Ile | Asp | Thr | Cys | Ile | Ser | Glu | Cys | Ile | Thr | Pro | Asn | Gly | Ser | Ile | |
| | | 290 | | | | | 295 | | | | | 300 | | | | |

| ccc | aat | gac | aag | ccc | ttc | caa | aat | gta | aac | aag | atc | aca | tac | gga | gca | 960 |
|---|---|---|---|---|---|---|---|---|---|---|---|---|---|---|---|---|
| Pro | Asn | Asp | Lys | Pro | Phe | Gln | Asn | Val | Asn | Lys | Ile | Thr | Tyr | Gly | Ala | |
| 305 | | | | | 310 | | | | | 315 | | | | | 320 | |

| tgt | ccc | aaa | tat | gtt | aag | caa | aac | acc | ttg | aaa | ctg | gca | aca | gga | atg | 1008 |
|---|---|---|---|---|---|---|---|---|---|---|---|---|---|---|---|---|
| Cys | Pro | Lys | Tyr | Val | Lys | Gln | Asn | Thr | Leu | Lys | Leu | Ala | Thr | Gly | Met | |
| | | | | 325 | | | | | 330 | | | | | 335 | | |

| cgg | aat | gtc | cct | gag | agg | caa | acc | aga | ggc | ctg | ttc | ggc | gca | ata | gca | 1056 |
|---|---|---|---|---|---|---|---|---|---|---|---|---|---|---|---|---|
| Arg | Asn | Val | Pro | Glu | Arg | Gln | Thr | Arg | Gly | Leu | Phe | Gly | Ala | Ile | Ala | |
| | | | 340 | | | | | 345 | | | | | 350 | | | |

| ggt | ttc | ata | gaa | aat | gga | tgg | gaa | ggg | atg | gta | gac | ggt | tgg | tat | ggc | 1104 |
|---|---|---|---|---|---|---|---|---|---|---|---|---|---|---|---|---|
| Gly | Phe | Ile | Glu | Asn | Gly | Trp | Glu | Gly | Met | Val | Asp | Gly | Trp | Tyr | Gly | |
| | | | | 355 | | | | | 360 | | | | | 365 | | |

| ttc | agg | cac | caa | aat | tcc | gaa | ggt | aca | gga | caa | gca | gca | gac | ctt | aaa | 1152 |
|---|---|---|---|---|---|---|---|---|---|---|---|---|---|---|---|---|
| Phe | Arg | His | Gln | Asn | Ser | Glu | Gly | Thr | Gly | Gln | Ala | Ala | Asp | Leu | Lys | |
| | | 370 | | | | | 375 | | | | | 380 | | | | |

| agc | act | cag | gca | gcc | att | gac | cag | att | aat | ggg | aaa | ttg | aac | aga | gtg | 1200 |

```
                                                               -continued
Ser Thr Gln Ala Ala Ile Asp Gln Ile Asn Gly Lys Leu Asn Arg Val
385                 390                 395                 400 att gaa aaa acg aat gag aag ttc cat caa atc gaa aag gag ttt tcc         1248
Ile Glu Lys Thr Asn Glu Lys Phe His Gln Ile Glu Lys Glu Phe Ser
                    405                 410                 415 gaa gta gaa ggg agg att caa gac ctt gag aga tac gtt gaa gac aca         1296
Glu Val Glu Gly Arg Ile Gln Asp Leu Glu Arg Tyr Val Glu Asp Thr
                420                 425                 430 aaa gta gat ctt tgg tct tac aat gcc gag ctt ctt gtt gct tta gaa         1344
Lys Val Asp Leu Trp Ser Tyr Asn Ala Glu Leu Leu Val Ala Leu Glu
            435                 440                 445 aac cag aaa aca att gat tta act gat tca gaa atg aac aaa ttg ttt         1392
Asn Gln Lys Thr Ile Asp Leu Thr Asp Ser Glu Met Asn Lys Leu Phe
        450                 455                 460 gaa aag act agg agg caa ttg agg gaa aat gct gaa gac atg ggc aat         1440
Glu Lys Thr Arg Arg Gln Leu Arg Glu Asn Ala Glu Asp Met Gly Asn
465                 470                 475                 480 ggc tgc ttc aag ata tac cac aag tgt gac aat gct tgc ata gaa tcg         1488
Gly Cys Phe Lys Ile Tyr His Lys Cys Asp Asn Ala Cys Ile Glu Ser
                    485                 490                 495 att aga aac gga act tat gac cat aac ata tat aga gat gag gca gtg         1536
Ile Arg Asn Gly Thr Tyr Asp His Asn Ile Tyr Arg Asp Glu Ala Val
                500                 505                 510 aac aat cgg ttc cag atc aaa ggt gtt gag cta aag tct gga tac aaa         1584
Asn Asn Arg Phe Gln Ile Lys Gly Val Glu Leu Lys Ser Gly Tyr Lys
            515                 520                 525 gac tgg atc ttg tgg att tcc ttt gcc ata tca tgc ttt ttg ctt tgt         1632
Asp Trp Ile Leu Trp Ile Ser Phe Ala Ile Ser Cys Phe Leu Leu Cys
        530                 535                 540 gtt gtc ttg ctg ggt ttc att atg tgg gcc tgc cag aga ggc aac att         1680
Val Val Leu Leu Gly Phe Ile Met Trp Ala Cys Gln Arg Gly Asn Ile
545                 550                 555                 560 agg tgc aac att tgc att tga                                             1701
Arg Cys Asn Ile Cys Ile
                    565

<210> SEQ ID NO 10
<211> LENGTH: 566
<212> TYPE: PRT
<213> ORGANISM: Artificial Sequence
<220> FEATURE:
<223> OTHER INFORMATION: HA amino acid of A/Canine/Korea/01/07(H3N2)

<400> SEQUENCE: 10

Met Lys Thr Val Ile Ala Leu Ser Tyr Ile Phe Cys Leu Ala Phe Gly
 1               5                  10                  15

Gln Asn Leu Pro Gly Asn Glu Asn Asn Ala Ala Thr Leu Cys Leu Gly
             20                  25                  30

His His Ala Val Pro Asn Gly Thr Ile Val Lys Thr Ile Thr Asp Asp
         35                  40                  45

Gln Ile Glu Val Thr Asn Ala Thr Glu Leu Val Gln Asn Ser Ser Thr
     50                  55                  60

Gly Lys Ile Cys Asn Asn Pro His Lys Ile Leu Asp Gly Arg Asp Cys
 65                  70                  75                  80

Thr Leu Ile Asp Ala Leu Leu Gly Asp Pro His Cys Asp Val Phe Gln
                 85                  90                  95

Asn Glu Thr Trp Asp Leu Phe Val Glu Arg Ser Asn Ala Phe Ser Asn
            100                 105                 110

Cys Tyr Pro Tyr Asp Val Pro Asp Tyr Ala Ser Leu Arg Ser Ile Val
        115                 120                 125
```

```
Ala Ser Ser Gly Thr Leu Glu Phe Ile Thr Glu Gly Phe Thr Trp Thr
    130                 135                 140
Gly Val Thr Gln Asn Gly Gly Ser Gly Ala Cys Lys Arg Gly Pro Ala
145                 150                 155                 160
Asn Gly Phe Phe Ser Arg Leu Asn Trp Leu Thr Lys Ser Gly Asn Thr
                165                 170                 175
Tyr Pro Val Leu Asn Val Thr Met Pro Asn Asn Asn Asn Phe Asp Lys
            180                 185                 190
Leu Tyr Ile Trp Gly Val His His Pro Ser Thr Asn Gln Glu Gln Thr
        195                 200                 205
Ser Leu Tyr Ile Gln Ala Ser Gly Arg Val Thr Val Ser Thr Arg Arg
    210                 215                 220
Ser Gln Gln Thr Ile Ile Pro Asn Ile Gly Ser Arg Pro Leu Val Arg
225                 230                 235                 240
Gly Gln Ser Gly Arg Ile Ser Val Tyr Trp Thr Ile Val Lys Pro Gly
                245                 250                 255
Asp Val Leu Val Ile Asn Ser Asn Gly Asn Leu Ile Ala Pro Arg Gly
            260                 265                 270
Tyr Phe Lys Met Arg Ile Gly Lys Ser Ser Ile Met Arg Ser Asp Ala
        275                 280                 285
Pro Ile Asp Thr Cys Ile Ser Glu Cys Ile Thr Pro Asn Gly Ser Ile
    290                 295                 300
Pro Asn Asp Lys Pro Phe Gln Asn Val Asn Lys Ile Thr Tyr Gly Ala
305                 310                 315                 320
Cys Pro Lys Tyr Val Lys Gln Asn Thr Leu Lys Leu Ala Thr Gly Met
                325                 330                 335
Arg Asn Val Pro Glu Arg Gln Thr Arg Gly Leu Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Thr Gly Gln Ala Ala Asp Leu Lys
    370                 375                 380
Ser Thr Gln Ala Ala Ile Asp Gln Ile Asn Gly Lys Leu Asn Arg Val
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Arg Tyr Val Glu Asp Thr
            420                 425                 430
Lys Val Asp Leu Trp Ser Tyr Asn Ala Glu Leu Leu Val Ala Leu Glu
        435                 440                 445
Asn Gln Lys Thr Ile Asp Leu Thr Asp Ser Glu Met Asn Lys Leu Phe
    450                 455                 460
Glu Lys Thr Arg Arg Gln Leu Arg Glu Asn Ala Glu Asp Met Gly Asn
465                 470                 475                 480
Gly Cys Phe Lys Ile Tyr His Lys Cys Asp Asn Ala Cys Ile Glu Ser
                485                 490                 495
Ile Arg Asn Gly Thr Tyr Asp His Asn Ile Tyr Arg Asp Glu Ala Val
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
    530                 535                 540
Val Val Leu Leu Gly Phe Ile Met Trp Ala Cys Gln Arg Gly Asn Ile
```

<210> SEQ ID NO 11
<211> LENGTH: 1410
<212> TYPE: DNA
<213> ORGANISM: Artificial Sequence
<220> FEATURE:
<223> OTHER INFORMATION: NA full gene of A/Canine/Korea/01/07(H3N2)
<220> FEATURE:
<221> NAME/KEY: CDS
<222> LOCATION: (1)..(1407)
<223> OTHER INFORMATION: NA amino acid of A/Canine/Korea/01/07(H3N2)

<400> SEQUENCE: 11

```
atg aac cca aat cag aag ata ata gca ata ggc tct gtc tct cta acc      48
Met Asn Pro Asn Gln Lys Ile Ile Ala Ile Gly Ser Val Ser Leu Thr
  1               5                  10                  15 att gca aca gta tgt ttc ctc ttg cag att gcc atc cta gca aca act      96
Ile Ala Thr Val Cys Phe Leu Leu Gln Ile Ala Ile Leu Ala Thr Thr
             20                  25                  30 gtg aca ctg cac ttc aag caa aat gaa tgc aac atc ccc tcg aac agt     144
Val Thr Leu His Phe Lys Gln Asn Glu Cys Asn Ile Pro Ser Asn Ser
         35                  40                  45 caa gta gtg cca tgt aaa cca atc ata ata gaa agg aac ata aca gag     192
Gln Val Val Pro Cys Lys Pro Ile Ile Ile Glu Arg Asn Ile Thr Glu
     50                  55                  60 gta gta tat ttg aat aat act acc ata gaa aaa gaa att tgt tcc ata     240
Val Val Tyr Leu Asn Asn Thr Thr Ile Glu Lys Glu Ile Cys Ser Ile
 65                  70                  75                  80 gtg cta gaa tac agg aac tgg tcg aag ccg cag tgt caa att aca gga     288
Val Leu Glu Tyr Arg Asn Trp Ser Lys Pro Gln Cys Gln Ile Thr Gly
                 85                  90                  95 ttt gct cct ttc tcc aag gac aac tca atc cga ctc tcc gct ggt ggg     336
Phe Ala Pro Phe Ser Lys Asp Asn Ser Ile Arg Leu Ser Ala Gly Gly
            100                 105                 110 gac att tgg gta aca agg gaa cct tat gtg tca tgc gac ccc agc aaa     384
Asp Ile Trp Val Thr Arg Glu Pro Tyr Val Ser Cys Asp Pro Ser Lys
        115                 120                 125 tgt tac cag ttt gca ctt ggg cag ggg acc acg ctg aac aat aaa cac     432
Cys Tyr Gln Phe Ala Leu Gly Gln Gly Thr Thr Leu Asn Asn Lys His
    130                 135                 140 tca aac ggc aca ata cat gat agg atc tct cat cga act ctt tta atg     480
Ser Asn Gly Thr Ile His Asp Arg Ile Ser His Arg Thr Leu Leu Met
145                 150                 155                 160 aat gag ttg ggt gtt ccg ttt cat ttg gga acc aaa caa gtg tgc ata     528
Asn Glu Leu Gly Val Pro Phe His Leu Gly Thr Lys Gln Val Cys Ile
                165                 170                 175 gca tgg tcc agt tca agt tgt cac gat ggg aaa gca tgg tta cat gtt     576
Ala Trp Ser Ser Ser Ser Cys His Asp Gly Lys Ala Trp Leu His Val
            180                 185                 190 tgt gtc act ggg gat gat aga aat gcg act gct agt ttc gtt tat aat     624
Cys Val Thr Gly Asp Asp Arg Asn Ala Thr Ala Ser Phe Val Tyr Asn
        195                 200                 205 gga atg ctt gtt gac agt att ggt tca tgg tct cga aat atc ctc aga     672
Gly Met Leu Val Asp Ser Ile Gly Ser Trp Ser Arg Asn Ile Leu Arg
    210                 215                 220 act cag gag tca gaa tgc gtt tgc atc aat gga act tgt aca gta gta     720
Thr Gln Glu Ser Glu Cys Val Cys Ile Asn Gly Thr Cys Thr Val Val
225                 230                 235                 240 atg act gat gga agt gca tca gga agg gct gat act aga ata cta ttc     768
```

```
                Met Thr Asp Gly Ser Ala Ser Gly Arg Ala Asp Thr Arg Ile Leu Phe
                                245                 250                 255 atc aga gag ggg aaa att gtc cat att agc cca ttg tca ggg agt gct         816
Ile Arg Glu Gly Lys Ile Val His Ile Ser Pro Leu Ser Gly Ser Ala
            260                 265                 270 caa cat ata gag gaa tgt tcc tgt tat cct cga tat cca aat gtt aga         864
Gln His Ile Glu Glu Cys Ser Cys Tyr Pro Arg Tyr Pro Asn Val Arg
        275                 280                 285 tgt gtt tgc aga gac aat tgg aag ggc tct aat agg ccc gtt ata gat         912
Cys Val Cys Arg Asp Asn Trp Lys Gly Ser Asn Arg Pro Val Ile Asp
    290                 295                 300 ata aat atg gca gat tat agc atc gat tcc agt tat gtg tgt tca gga        960
Ile Asn Met Ala Asp Tyr Ser Ile Asp Ser Ser Tyr Val Cys Ser Gly
305                 310                 315                 320 ctt gtt ggc gac aca cca agg aat gat gat agc tct agc agc agc aac       1008
Leu Val Gly Asp Thr Pro Arg Asn Asp Asp Ser Ser Ser Ser Ser Asn
                325                 330                 335 tgc agg gat cct aat aat gag aga ggg aat cca gga gtg aaa ggg tgg       1056
Cys Arg Asp Pro Asn Asn Glu Arg Gly Asn Pro Gly Val Lys Gly Trp
            340                 345                 350 gct ttt gat aat gag aat gac gtt tgg atg ggg agg aca atc agc aaa       1104
Ala Phe Asp Asn Glu Asn Asp Val Trp Met Gly Arg Thr Ile Ser Lys
        355                 360                 365 gat ttg cgc tca ggt tat gag act ttc aag gtc att ggt ggc tgg acc       1152
Asp Leu Arg Ser Gly Tyr Glu Thr Phe Lys Val Ile Gly Gly Trp Thr
    370                 375                 380 act gct aat tcc aag tta cag gtc aat aga caa gtc ata gtc gat aat       1200
Thr Ala Asn Ser Lys Leu Gln Val Asn Arg Gln Val Ile Val Asp Asn
385                 390                 395                 400 aat aac tgg tct ggt tat tct ggt att ttc tcc gtt gaa ggc aaa agc       1248
Asn Asn Trp Ser Gly Tyr Ser Gly Ile Phe Ser Val Glu Gly Lys Ser
                405                 410                 415 tgt gtt aat agg tgt ttt tat gtg gag ttg ata aga gga ggg cca caa       1296
Cys Val Asn Arg Cys Phe Tyr Val Glu Leu Ile Arg Gly Gly Pro Gln
            420                 425                 430 gag act aga gta tgg tgg act tca aat agc att gtc gta ttt tgt ggt       1344
Glu Thr Arg Val Trp Trp Thr Ser Asn Ser Ile Val Val Phe Cys Gly
        435                 440                 445 act tct ggt acc tat gga aca ggc tca tgg cct gat ggg gcg aat atc       1392
Thr Ser Gly Thr Tyr Gly Thr Gly Ser Trp Pro Asp Gly Ala Asn Ile
    450                 455                 460 aac ttc atg cct ata taa                                                1410
Asn Phe Met Pro Ile
465

<210> SEQ ID NO 12
<211> LENGTH: 469
<212> TYPE: PRT
<213> ORGANISM: Artificial Sequence
<220> FEATURE:
<223> OTHER INFORMATION: NA amino acid of A/Canine/Korea/01/07(H3N2)

<400> SEQUENCE: 12

Met Asn Pro Asn Gln Lys Ile Ile Ala Ile Gly Ser Val Ser Leu Thr
1               5                   10                  15

Ile Ala Thr Val Cys Phe Leu Leu Gln Ile Ala Ile Leu Ala Thr Thr
            20                  25                  30

Val Thr Leu His Phe Lys Gln Asn Glu Cys Asn Ile Pro Ser Asn Ser
        35                  40                  45

Gln Val Val Pro Cys Lys Pro Ile Ile Ile Glu Arg Asn Ile Thr Glu
    50                  55                  60
```

```
Val Val Tyr Leu Asn Asn Thr Thr Ile Glu Lys Glu Ile Cys Ser Ile
 65                  70                  75                  80

Val Leu Glu Tyr Arg Asn Trp Ser Lys Pro Gln Cys Gln Ile Thr Gly
                 85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Ser Lys
        115                 120                 125

Cys Tyr Gln Phe Ala Leu Gly Gln Gly Thr Thr Leu Asn Asn Lys His
    130                 135                 140

Ser Asn Gly Thr Ile His Asp Arg Ile Ser His Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Arg Asn Ala Thr Ala Ser Phe Val Tyr Asn
        195                 200                 205

Gly Met Leu Val Asp Ser Ile Gly Ser Trp Ser Arg Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
            245                 250                 255

Ile Arg Glu Gly Lys Ile Val His Ile Ser Pro Leu Ser Gly Ser Ala
        260                 265                 270

Gln His Ile Glu Glu Cys Ser Cys Tyr Pro Arg Tyr Pro Asn Val Arg
    275                 280                 285

Cys Val Cys Arg Asp Asn Trp Lys Gly Ser Asn Arg Pro Val Ile Asp
290                 295                 300

Ile Asn Met Ala Asp Tyr Ser Ile Asp Ser Ser Tyr Val Cys Ser Gly
305                 310                 315                 320

Leu Val Gly Asp Thr Pro Arg Asn Asp Asp Ser Ser Ser Ser Ser Asn
            325                 330                 335

Cys Arg Asp Pro Asn Asn Glu Arg Gly Asn Pro Gly Val Lys Gly Trp
        340                 345                 350

Ala Phe Asp Asn Glu Asn Asp Val Trp Met Gly Arg Thr Ile Ser Lys
    355                 360                 365

Asp Leu Arg Ser Gly Tyr Glu Thr Phe Lys Val Ile Gly Gly Trp Thr
370                 375                 380

Thr Ala Asn Ser Lys Leu Gln Val Asn Arg Gln Val Ile Val Asp Asn
385                 390                 395                 400

Asn Asn Trp Ser Gly Tyr Ser Gly Ile Phe Ser Val Glu Gly Lys Ser
            405                 410                 415

Cys Val Asn Arg Cys Phe Tyr Val Glu Leu Ile Arg Gly Gly Pro Gln
        420                 425                 430

Glu Thr Arg Val Trp Trp Thr Ser Asn Ser Ile Val Val Phe Cys Gly
    435                 440                 445

Thr Ser Gly Thr Tyr Gly Thr Gly Ser Trp Pro Asp Gly Ala Asn Ile
450                 455                 460

Asn Phe Met Pro Ile
465
```

<210> SEQ ID NO 13
<211> LENGTH: 722
<212> TYPE: DNA
<213> ORGANISM: Artificial Sequence
<220> FEATURE:
<223> OTHER INFORMATION: HA partial gene of A/Canine/Korea/02/07(H3N2)

<400> SEQUENCE: 13

```
cagattgagg tgactaatgc caccgagcta gtccaaaact cctcaacagg gaaaatatgc      60
aacaatcccc acaagatcct tgatgggagg gactgcacac taatagatgc cctactaggg     120
gacccgcact gtgatgtctt ccaaaatgag acatgggacc tttttgtgga acgaagcaat     180
gcttttagca attgttaccc ttatgatgta ccagactatg catcccttcg atccatagtt     240
gcatcatcag gcacattgga gttcatcact gaaggtttca cttgggcagg agtaactcaa     300
aatggaggaa gcggtgcttg caaaaggga cctgctaatg gtttcttcag cagattgaat     360
tggttaacta agtcaggaaa tacatatcca gtgttgaatg tgactatgcc aaacaataac     420
aatttcgaca aattatacat ttggggagtt tatcacccaa gcactaatca agaacaaacc     480
agcctgtata ttcaggcctc aggaagagtc acagtctcta ccaggagaag ccaacagacc     540
ataatcccaa acattggatc tagacccttg gtaaggggcc aatctggcag aataagtgta     600
tattggacaa tagtcaaacc tggagacgta ctggtaataa acagtaatag aaacctaatc     660
gctcctcgag gctacttcaa aatgcgcatt gggaaaagct caataatgag atcagatgca     720
cc                                                                    722
```

<210> SEQ ID NO 14
<211> LENGTH: 477
<212> TYPE: DNA
<213> ORGANISM: Artificial Sequence
<220> FEATURE:
<223> OTHER INFORMATION: NA partial gene of A/Canine/Korea/02/07(H3N2)

<400> SEQUENCE: 14

```
ccaacaagcc ctgaacacac ataactggaa tcgatgctat aatctgccat atttatatct      60
ataacgggcc tattagagcc cttccaattg tctctgcaaa cacatctaac atttggatat     120
cgaggataac aggaacattc ctctatatgt tgagcactcc ctgacaatgg gctaatatgg     180
acaattttcc cctctctgat gaatagtatt ctagtatcag cccttcctga tgcacttcca     240
tcagtcatta ctactgtaca agttccattg atgcaaacgc attctgactc ctgagttctg     300
aggatatttc gagaccatga accaatactg tcaacaagca ttccattata acgaaaacta     360
gcagtcgcat ttctatcatc cccagtgaca caaacatgta accatgcttt cccatcgtga     420
caacttgaac tggaccatgc tatgcacact tgtttggttc caaatgaaa cggaaca        477
```

<210> SEQ ID NO 15
<211> LENGTH: 722
<212> TYPE: DNA
<213> ORGANISM: Artificial Sequence
<220> FEATURE:
<223> OTHER INFORMATION: HA partial gene of A/Canine/Korea/03/07(H3N2)

<400> SEQUENCE: 15

```
cagattgagg tgaccaatgc caccgagcta gtccaaaact cctcaacagg gaaaatatgc      60
aacaatcccc acaagatcct tgatgggagg gactgcacac taatagatgc cctactaggg     120
gacccgcact gtgatgtctt ccaaaatgag acatgggacc tttttgtgga acgaagcaat     180
gcttttagca attgttaccc ttatgatgta ccagactatg catcccttcg atccatagtt     240
gcatcatcag gcacattgga gttcatcgct gaaggtttca cttgggcagg agtaactcaa     300
```

```
aatggaggaa gcggtgcttg caaaagggga cctgctaatg gtttcttcag cagattgaat      360
tggttaacta agtcaggaaa tacatatcca gtgttgaatg tgactatgcc aaacaataac      420
aatttcgaca aattatacat ttggggagtt catcacccaa gcactaatca agaacaaacc      480
agcctgtata ttcaggcctc aggaagagtc acagtctcta ccaggagaag ccaacagacc      540
ataatcccaa acattggatc tagacccttg gtaaggggcc aatctggcag aataagtgta      600
tattggacaa tagtcaaacc tggggacgta ctggtaataa acagtaatgg aaacctaatc      660
gctcctcgag gctacttcaa aatgcgcatt gggaaaagct caataatgag atcagatgca      720
cc                                                                     722
```

```
<210> SEQ ID NO 16
<211> LENGTH: 477
<212> TYPE: DNA
<213> ORGANISM: Artificial Sequence
<220> FEATURE:
<223> OTHER INFORMATION: NA partial gene of A/Canine/Korea/03/07(H3N2)

<400> SEQUENCE: 16
ccaacaagcc ctgaacacac ataactggaa tcgatgctat aatctgccat atttatatct       60
ataacgggcc tattagagcc cttccaattg tctctgcaaa cacatctaac atttggatat      120
cgaggataac aggaacattc ctctatatgt tgagcactcc ctgacaatgg gctaatatgg      180
acaattttcc cctctctgat gaatagtatt ctagtatcag cccttcctga tgcacttcca      240
tcagtcatta ctactgtaca agttccattg atgcaaacgc attctgactc ctgagttctg      300
aggatatttc gagaccatga accaatactg tcaacaagca ttccattata aacgaaacta      360
gcagtcgcat ttctatcatc cccagtgaca caaacatgta accatgcttt cccatcgtga      420
caacttgaac tggaccatgc tatgcacact tgtttggttc ccaaatgaaa cggaaca        477
```

```
<210> SEQ ID NO 17
<211> LENGTH: 20
<212> TYPE: DNA
<213> ORGANISM: Artificial Sequence
<220> FEATURE:
<223> OTHER INFORMATION: primer for H3

<400> SEQUENCE: 17
carattgarg tgachaatgc                                                   20
```

```
<210> SEQ ID NO 18
<211> LENGTH: 19
<212> TYPE: DNA
<213> ORGANISM: Artificial Sequence
<220> FEATURE:
<223> OTHER INFORMATION: primer for H3

<400> SEQUENCE: 18
ggtgcatctg ayctcatta                                                    19
```

```
<210> SEQ ID NO 19
<211> LENGTH: 20
<212> TYPE: DNA
<213> ORGANISM: Artificial Sequence
<220> FEATURE:
<223> OTHER INFORMATION: primer for N2

<400> SEQUENCE: 19
tgttccgttt catttgggaa                                                   20
```

-continued

```
<210> SEQ ID NO 20
<211> LENGTH: 20
<212> TYPE: DNA
<213> ORGANISM: Artificial Sequence
<220> FEATURE:
<223> OTHER INFORMATION: primer for N2

<400> SEQUENCE: 20
ccaacaagcc ctgaacacac                                              20

<210> SEQ ID NO 21
<211> LENGTH: 20
<212> TYPE: DNA
<213> ORGANISM: Artificial Sequence
<220> FEATURE:
<223> OTHER INFORMATION: primer for PB1

<400> SEQUENCE: 21
aaagtgccag cacaaaatgc                                              20

<210> SEQ ID NO 22
<211> LENGTH: 20
<212> TYPE: DNA
<213> ORGANISM: Artificial Sequence
<220> FEATURE:
<223> OTHER INFORMATION: primer for PB1

<400> SEQUENCE: 22
ttctcacaga tgctcctcgc                                              20

<210> SEQ ID NO 23
<211> LENGTH: 20
<212> TYPE: DNA
<213> ORGANISM: Artificial Sequence
<220> FEATURE:
<223> OTHER INFORMATION: primer for PB2

<400> SEQUENCE: 23
tcatggaggt cgttttttcca                                             20

<210> SEQ ID NO 24
<211> LENGTH: 20
<212> TYPE: DNA
<213> ORGANISM: Artificial Sequence
<220> FEATURE:
<223> OTHER INFORMATION: primer for PB2

<400> SEQUENCE: 24
tgaatcagcc ttctggttgc                                              20

<210> SEQ ID NO 25
<211> LENGTH: 20
<212> TYPE: DNA
<213> ORGANISM: Artificial Sequence
<220> FEATURE:
<223> OTHER INFORMATION: primer for PA

<400> SEQUENCE: 25
gaagtgagcg ccaaaattga                                              20

<210> SEQ ID NO 26
<211> LENGTH: 20
<212> TYPE: DNA
<213> ORGANISM: Artificial Sequence
<220> FEATURE:
<223> OTHER INFORMATION: primer for PA

<400> SEQUENCE: 26
```

```
ctctggctca tcgctgtcat                                              20

<210> SEQ ID NO 27
<211> LENGTH: 20
<212> TYPE: DNA
<213> ORGANISM: Artificial Sequence
<220> FEATURE:
<223> OTHER INFORMATION: primer for NP

<400> SEQUENCE: 27
acggtctgca ctcatcctga                                              20

<210> SEQ ID NO 28
<211> LENGTH: 20
<212> TYPE: DNA
<213> ORGANISM: Artificial Sequence
<220> FEATURE:
<223> OTHER INFORMATION: primer for NP

<400> SEQUENCE: 28
gcccctggaa agacacatct                                              20

<210> SEQ ID NO 29
<211> LENGTH: 20
<212> TYPE: DNA
<213> ORGANISM: Artificial Sequence
<220> FEATURE:
<223> OTHER INFORMATION: primer for M

<400> SEQUENCE: 29
aacattccat ggggctaagg                                              20

<210> SEQ ID NO 30
<211> LENGTH: 20
<212> TYPE: DNA
<213> ORGANISM: Artificial Sequence
<220> FEATURE:
<223> OTHER INFORMATION: primer for M

<400> SEQUENCE: 30
cggcaataac gagaggatca                                              20

<210> SEQ ID NO 31
<211> LENGTH: 20
<212> TYPE: DNA
<213> ORGANISM: Artificial Sequence
<220> FEATURE:
<223> OTHER INFORMATION: primer for NS

<400> SEQUENCE: 31
gactggttca tgctcatgcc                                              20

<210> SEQ ID NO 32
<211> LENGTH: 20
<212> TYPE: DNA
<213> ORGANISM: Artificial Sequence
<220> FEATURE:
<223> OTHER INFORMATION: primer for NS

<400> SEQUENCE: 32
gagagagtga aggtccccca                                              20
```